(12) United States Patent
Galzi et al.

(10) Patent No.: US 7,202,046 B2
(45) Date of Patent: Apr. 10, 2007

(54) USE OF A FLUORESCENT PROTEIN FOR DETECTING INTERACTION BETWEEN A TARGET PROTEIN AND ITS LIGAND

(75) Inventors: Jean-Luc Galzi, Strasbourg (FR); Philippe Alix, Carpiquet (FR)

(73) Assignee: Centre National de la Recherche Scientifique (C.N.R.S.), Paris (FR)

( * ) Notice: Subject to any disclaimer, the term of this patent is extended or adjusted under 35 U.S.C. 154(b) by 341 days.

(21) Appl. No.: 10/776,330

(22) Filed: Feb. 12, 2004

(65) Prior Publication Data
US 2005/0059036 A1    Mar. 17, 2005

Related U.S. Application Data

(63) Continuation of application No. 09/445,205, filed as application No. PCT/FR98/01136 on Jun. 4, 1998, now abandoned.

(30) Foreign Application Priority Data
Jun. 5, 1997    (FR)    .................... 97 06977

(51) Int. Cl.
| | |
|---|---|
| G01N 33/53 | (2006.01) |
| C12Q 1/68 | (2006.01) |
| C12N 15/63 | (2006.01) |
| C07H 21/04 | (2006.01) |
| G01N 33/567 | (2006.01) |

(52) U.S. Cl. .................. 435/7.8; 435/6; 435/320.1; 536/23.1; 536/23.4

(58) Field of Classification Search ............... None
See application file for complete search history.

(56) References Cited

U.S. PATENT DOCUMENTS 5,342,789 A    8/1994    Chick et al.
5,439,797 A    8/1995    Tsien et al.
5,625,048 A    4/1997    Tsien et al.

FOREIGN PATENT DOCUMENTS

| EP | 0 552 108 | 7/1993 |
|---|---|---|
| WO | 91/01305 | 2/1991 |
| WO | 96/41166 | 12/1996 |
| WO | 97/28261 | 8/1997 |

OTHER PUBLICATIONS

Atsushi Miyawaki et al., "Fluorescent Indicators for $Ca^{2+}$ Based onGreen Fluorescent Porteins and Calmodulin," Letters to Nature, vol. 388, Aug. 1997, pp. 882-887.
Valerie A. Romoser et al., "Detection in Living Cells of $Ca^{2+}$—dependent changes in the Fluorescene . . ." The Journal of Biological Chemistry, vol. 272, No. 20, 1997, pp. 13270-13274.
Valentin N. Petushkov et al., "Direct Measurement of Excitation Transfer in the Protein Complex of Bacterial Luciferase . . ." Biochemistry, vol. 35, No. 25, 1996, pp. 8413-8418.
Robi D. Mitra et al., "Fluorence Resonance Energy Transfer Between Blue-Emitting and Red-Shifted Excitation . . ." Gene, vol. 173, No. 1, 1996, pp. 13-17.

*Primary Examiner*—David Guzo
*Assistant Examiner*—Michele K. Joike
(74) *Attorney, Agent, or Firm*—Young & Thompson

(57) ABSTRACT

The invention relates to the use of a fluorescent protein chosen in particular from autofluorescent proteins,
  for the detection of the non-covalent interactions between a target protein labeled with the fluorescent protein and one of its ligands labeled with a label consisting:
    either of a molecule which is capable of absorbing the light emitted by the fluorescent protein,
    or of a fluorescent substance,
this detection taking place by fluorescence energy transfer:
  between the fluorescent protein and the above-mentioned fluorescent substance, the fluorescent substance being such that either it is excitable at the emission wavelength of the fluorescent protein, or it emits at the excitation wavelength of the fluorescent protein, or
  between the fluorescent protein and the above-mentioned molecule which is capable of absorbing the light emitted by the fluorescent protein.

19 Claims, 18 Drawing Sheets

Figure 1

SEQUENCE LISTING

<160> NUMBER OF SEQ ID NOS: 25

<210> SEQ ID NO 1
<211> LENGTH: 798
<212> TYPE: DNA
<213> ORGANISM: Aequorea Victoria
<220> FEATURE:
<221> NAME/KEY: CDS
<222> LOCATION: (1)..(795)

<400> SEQUENCE: 1

```
atg gtg agc aag ggc gag gag ctg ttc acc ggg gtg gtg ccc atc ctg      48
Met Val Ser Lys Gly Glu Glu Leu Phe Thr Gly Val Val Pro Ile Leu
  1               5                  10                  15 gtc gag ctg gac ggc gac gta aac ggc cac aag ttc agc gtg tcc ggc      96
Val Glu Leu Asp Gly Asp Val Asn Gly His Lys Phe Ser Val Ser Gly
             20                  25                  30 gag ggc gag ggc gat gcc acc tac ggc aag ctg acc ctg aag ttc atc     144
Glu Gly Glu Gly Asp Ala Thr Tyr Gly Lys Leu Thr Leu Lys Phe Ile
         35                  40                  45 tgc acc acc ggc aag ctg ccc gtg ccc tgg ccc acc ctc gtg acc acc     192
```

-continued

```
ctg acc tac ggc gtg cag tgc ttc agc cgc tac ccc aac cac atg aag      240
Leu Thr Tyr Gly Val Gln Cys Phe Ser Arg Tyr Pro Asp His Met Lys
 65                  70                  75                  80 cag cac gac ttc ttc aag tcc gcc atg ccc gaa ggc tac gtc cag gag      288
Gln His Asp Phe Phe Lys Ser Ala Met Pro Glu Gly Tyr Val Gln Glu
                 85                  90                  95 cgc acc atc ttc ttc aag gac gac ggc aac tac aag acc cgc gcc gag      336
Arg Thr Ile Phe Phe Lys Asp Asp Gly Asn Tyr Lys Thr Arg Ala Glu
            100                 105                 110 gtg aag ttc gag ggc gac acc ctg gtg aac cgc atc gag ctg aag ggc      384
Val Lys Phe Glu Gly Asp Thr Leu Val Asn Arg Ile Glu Leu Lys Gly
        115                 120                 125 atc gac ttc aag gag gac ggc aac atc ctg ggg cac aag ctg gag tac      432
Ile Asp Phe Lys Glu Asp Gly Asn Ile Leu Gly His Lys Leu Glu Tyr
    130                 135                 140 aac tac aac agc cac aac gtc tat atc atg gcc gac aag cag aag aac      480
Asn Tyr Asn Ser His Asn Val Tyr Ile Met Ala Asp Lys Gln Lys Asn
145                 150                 155                 160 ggc atc aag gtg aac ttc aag atc cgc cac aac atc gag gac ggc agc      528
Gly Ile Lys Val Asn Phe Lys Ile Arg His Asn Ile Glu Asp Gly Ser
                165                 170                 175 gtg cag ctc gcc gac cac tac cag cag aac acc ccc atc ggc gac ggc      576
Val Gln Leu Ala Asp His Tyr Gln Gln Asn Thr Pro Ile Gly Asp Gly
            180                 185                 190 ccc gtg ctg ctg ccc gac aac cac tac ctg agc acc cag tcc gcc ctg      624
Pro Val Leu Leu Pro Asp Asn His Tyr Leu Ser Thr Gln Ser Ala Leu
        195                 200                 205 agc aaa gac ccc aac gag aag cgc gat cac atg gtc ctg ctg gag ttc      672
Ser Lys Asp Pro Asn Glu Lys Arg Asp His Met Val Leu Leu Glu Phe
    210                 215                 220 gtg acc gcc gcc ggg atc act ctc ggc atg gac gag ctg tac aag tac      720
Val Thr Ala Ala Gly Ile Thr Leu Gly Met Asp Glu Leu Tyr Lys Tyr
225                 230                 235                 240 tca gat ctc gag ctc aag ctt cga att ctg cag tcg acg gta ccg cgg      768
Ser Asp Leu Glu Leu Lys Leu Arg Ile Leu Gln Ser Thr Val Pro Arg
                245                 250                 255 gcc cgg gat cca ccg gat cta gat aac tga                              798
Ala Arg Asp Pro Pro Asp Leu Asp Asn
            260                 265

<210> SEQ ID NO 2
<211> LENGTH: 265
<212> TYPE: PRT
<213> ORGANISM: Aequorea victoria

<400> SEQUENCE: 2

Met Val Ser Lys Gly Glu Glu Leu Phe Thr Gly Val Val Pro Ile Leu
 1               5                  10                  15

Val Glu Leu Asp Gly Asp Val Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
        50                  55                  60

Leu Thr Tyr Gly Val Gln Cys Phe Ser Arg Tyr Pro Asp His Met Lys
 65                  70                  75                  80

Gln His Asp Phe Phe Lys Ser Ala Met Pro Glu Gly Tyr Val Gln Glu
```

```
                     85                  90                  95
Arg Thr Ile Phe Phe Lys Asp Asp Gly Asn Tyr Lys Thr Arg Ala Glu
                100                 105                 110

Val Lys Phe Glu Gly Asp Thr Leu Val Asn Arg Ile Glu Leu Lys Gly
            115                 120                 125

Ile Asp Phe Lys Glu Asp Gly Asn Ile Leu Gly His Lys Leu Glu Tyr
        130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys Tyr
225                 230                 235                 240

Ser Asp Leu Glu Leu Lys Leu Arg Ile Leu Gln Ser Thr Val Pro Arg
                245                 250                 255

Ala Arg Asp Pro Pro Asp Leu Asp Asn
            260                 265

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: spacer
      sequence

<400> SEQUENCE: 3

Gly Gly Gly Gly Ser
1               5

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence:
      Cyclopeptide

<400> SEQUENCE: 4

Gln Trp Phe Gly Leu Met
1               5

<210> SEQ ID NO 5
<211> LENGTH: 29
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 5
ggtcgccacc ctgtacaaga agggcgagg                                    29

<210> SEQ ID NO 6
<211> LENGTH: 36
```

```
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 6
cacgagagga tgtacaacct cgagcgcaca gtcacc                                 36

<210> SEQ ID NO 7
<211> LENGTH: 44
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 7
gtacccagac accagctagc agatctgaag cttcgccatc aggc                         44

<210> SEQ ID NO 8
<211> LENGTH: 39
<212> TYPE: DNA
<213> ORGANISM: Artificial Sequence
<220> FEATURE:
<223> OTHER INFORMATION: Description of Artificial Sequence: Primer

<400> SEQUENCE: 8
ggagagttcc aactcgagaa aagaaagaag ggcgaggag                              39

<210> SEQ ID NO 9
<211> LENGTH: 36
<212> TYPE: DNA
<213> ORGANISM: Artificial Sequence
<220> FEATURE:
<223> OTHER INFORMATION: Description of Artificial Sequence: Primer

<400> SEQUENCE: 9
gtcagctgtt tctgcggcgc gctaagcctg ggcctt                                 36

<210> SEQ ID NO 10
<211> LENGTH: 51
<212> TYPE: DNA
<213> ORGANISM: Artificial Sequence
<220> FEATURE:
<223> OTHER INFORMATION: Description of Artificial Sequence: Primer

<400> SEQUENCE: 10
ttagttctaa actagcggcc gcactagtcc tccatgaaca cttcagcccc a                51

<210> SEQ ID NO 11
<211> LENGTH: 42
<212> TYPE: DNA
<213> ORGANISM: Artificial Sequence
<220> FEATURE:
<223> OTHER INFORMATION: Description of Artificial Sequence: Primer

<400> SEQUENCE: 11
cttgaaccta tagctagcct cgagtcagca ttggcgggag gg                          42

<210> SEQ ID NO 12
<211> LENGTH: 28
<212> TYPE: DNA
<213> ORGANISM: Artificial Sequence
<220> FEATURE:
<223> OTHER INFORMATION: Description of Artificial Sequence: Primer
```

-continued

```
<400> SEQUENCE: 12
cctgctgtct cagatctcat caccgtcc                                              28

<210> SEQ ID NO 13
<211> LENGTH: 47
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 13
cagatcatta gttgtacagg aaagatcttg aggatcctgg agtgaag                         47

<210> SEQ ID NO 14
<211> LENGTH: 29
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 14
ggcccaagct tatgtcagga tccggggat                                             29

<210> SEQ ID NO 15
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 15
cgcccgctcg agtcacaagc ccacagatat                                            30

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 16
gttgacaagc ttcgggatcc a                                                     21

<210> SEQ ID NO 17
<211> LENGTH: 78
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 17
agcacagagg gcagtagcaa tgaggatgac agcgaggcgt gccgcggaga ccttcattgg           60
atcccgaagc ttatcaac                                                         78

<210> SEQ ID NO 18
<211> LENGTH: 78
<212> TYPE: DNA
<213> ORGANISM: Artificial Sequence
<220> FEATURE:
<223> OTHER INFORMATION: Description of Artificial Sequence:
      Oligonucleotide
```

```
<400> SEQUENCE: 18
attgctactg ccctctgtgc tcctgcatct gcctccccat attcctcgga caccacacca        60
tgctgcttcg cctacatt                                                     78

<210> SEQ ID NO 19
<211> LENGTH: 78
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 19
gcacttgcca ctggtgtaga aatactcctt gatgtgggca caaggcagtg ggcgggcaat        60
gtaggcgaag cagcatgg                                                     78

<210> SEQ ID NO 20
<211> LENGTH: 78
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 20
gcacttgcca ctggtgtaga aatactcctt gatgtgggca cggggcagtg ggcgagcaat        60
gtaggcaaag cagcatgg                                                     78

<210> SEQ ID NO 21
<211> LENGTH: 69
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 21
ctagctcatc tccagcgagt tgatgtactc ccgaacccat ttcttctctg ggttggcaca        60
aacttgacg                                                               69

<210> SEQ ID NO 22
<211> LENGTH: 50
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 22
aactcgctgg agatgagcta ggcggccgct cgaggtcgac ctagtcacta                   50

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 23
tagtgactag gtcgacctcg a                                                 21
```

-continued

```
<210> SEQ ID NO 24
<211> LENGTH: 41
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 24
gcggccgcat gggggatcct actctggagt ccatcatggc g                  41

<210> SEQ ID NO 25
<211> LENGTH: 43
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 25
ccgctcgagt taatctagaa ggaccaaatt gtactccttc aag                43
```

USE OF A FLUORESCENT PROTEIN FOR DETECTING INTERACTION BETWEEN A TARGET PROTEIN AND ITS LIGAND

This application is a continuation of application Ser. No. 09/445,205, filed on Jan. 7, 2000 now abandoned. Application Ser. No. 09/445,205 is the national phase of PCT International Application No. PCT/FR98/01136 filed on Jun. 4, 1998 under 35 U.S.C. § 371. The entire contents of each of the above-identified applications are hereby incorporated by reference.

The invention relates to the use of a fluorescent protein to detect interactions between a target protein and its ligand.

Many medicinal products and natural substances exert their action by interacting with regulatory proteins known as receptors, which are involved in many physiological functions of organisms, and impairment of their functions is the cause of many pathologies. The accessibility of the receptors to natural or synthetic, endogenous or exogenous pharmacological agents, from outside the cell, leads to them being considered as preferred targets in the search for biologically active molecules, in particular for molecules exhibiting potential therapeutic power.

In order to identify new pharmacological tools and medicinal products, a number of tests for screening biologically active molecules have been developed:

- the SPA test or scintillation proximity assay (Udenfirend et al., Anal. Biochem. (1987) 161: 494–500, U.S. Pat. No. 4,568,649; European Patent 0 154 734 and Japanese Patent Application Number 84//52452) does not make it possible to dispense with the use of radioactive molecules, and thus of all the inconveniences associated with the handling, use and storage of radioelements;
- the test of measurement by fluorescence energy transfer using the europium-allophycocyanine couple (Mathis. Clin. Chem. (1993), 39: 1953–1959) requires the use of purified allophycocyanine and requires it to be grafted onto a target protein which is also purified, although this is not always possible, especially when the target protein is not abundant;
- functional tests involving the regulation of reporter genes coding for luminescent proteins, or endowed with enzymatic activity assayed by colorinmetry, are very indirect measurements of the interaction between a ligand and its receptor, can be a source of false positives, involves amplification cascades which interfere with the quantitative measurement of the interactions between the receptor and its ligands, and are applicable only to biological systems coupled to a transcription of genes (Broach, J. R. & Thomer, J. 1996, Nature 384 supp. 14–16);
- a fluorescence measurement test allowing detection of the binding of an intracellular second messenger (the cyclic nucleotide cAMP) developed by grafting a second messenger binding site onto green fluorescent protein (GFP) from the jellyfish *Aequorea victoria* (Thastrup et al., WO 96/23898). This test, which allows the detection of biologically active molecules, is limited to analogues of second messengers which affect intracellular processes.

The gene coding for a fluorescent protein from the jellyfish *Aequorea victoria*, green fluorescent protein (or GFP) (Prasher et al. 1992, Gene 111: 229–233), has recently been decoded. GFP is a monomeric protein. It acquires its fluorescence properties by means of an autocatalytic mechanism of fluorophore formation. The endogenous or heterologous expression of GFP requires only one gene and does not need the addition of any prosthetic group. GFP has been expressed heterologously in cells and organisms as diverse as bacteria, yeasts and animal and plant eukaryotic cells. The structure of GFP (Ormö et al. 1996, Science 273: 1392–1395; Yang et al. 1996, Nature Biotechnology, 14: 1246–1251) allows it to be grafted onto other polypeptides, either on the amino-terminal or on the carboxy-terminal end without adversely affecting either its level of expression or the formation of the fluorophore. It is thus been possible to couple GFP, by gene fusion, with soluble or membrane proteins. Finally, the codons contained in the natural gene have been replaced with the preferred codons of the host organisms (EGFP [Cormack et al. 1996, Gene 173: 33–38] for example, for the expression in animal eukaryotic cells) and various mutations make it possible to modify its light absorption and emission spectra and allow multiple detections in a single expression system.

The invention relates, in particular, firstly to the preparation of target proteins, especially receptors, made fluorescent by fusion with a fluorescent protein, secondly to their labeled ligands, and to their use for the detection of interactions between the fluorescent receptors and their labeled ligands and the identification of novel biologically active molecules.

One of the other aspects of the invention is a process which is simple to implement, fast and sensitive for carrying out quantitative measurements, at equilibrium and in real-time, of non-covalent interactions between a target protein and its ligand.

One of the other aspects of the invention is to propose a process which can be generalized to many target proteins and their ligands.

One of the other aspects of the invention is to propose a process which does not require purification either of the target protein or of the ligand.

One of the aspects of the invention is to propose a process which is non-polluting, since it does not use radioactivity, is cost-effective, since it uses visible light (no quartz) on available equipment, and does not require any filtration.

One of the other aspects is to propose an automatable process.

The invention relates to the construction of cDNA containing a sequence coding for 1) a protein, in particular a receptor, in which one or more amino acids are substituted, inserted or deleted, fused with the cDNA coding for GFP, or one of its mutants, in which one or more amino acids are substituted, inserted or deleted in order to maintain the reading frame and to obtain a hybrid polypeptide.

The invention also relates to cells containing a DNA sequence coding for a protein, in particular a receptor, in which one or more amino acids are substituted, inserted or deleted, fused with the cDNA coding for GFP, or one of its mutants, in which one or more amino acids are substituted, inserted or deleted, in order to maintain the reading frame, and capable of expressing the DNA sequence considered.

The invention also relates to the production of pharmacologically active ligands containing a fluorescent chemical group linked via a chemical reaction, in which the fluorescent group is either a donor of energy to GFP or one of its mutants, or an acceptor of energy from GFP or one of its mutants.

The invention also relates to the culturing of cells containing the protein-GFP hybrid under conditions allowing 1) expression of the hybrid polypeptide,
2) detection of the fluorescence of the cell.

The invention also relates to the incubation of cells expressing the protein-GFP hybrid with the fluorescent ligand, the measurement of changes in the fluorescence either of donor emission or of acceptor emission, or of acceptor excitation, revealing the protein-ligand interaction, as well as the addition of a suspected biologically active molecule with the fluorescent ligand and the measurement of adverse changes in the energy transfer signal relative to the incubation of the above-mentioned cells with the fluorescent ligand.

The invention also relates to the construction of cDNA containing a sequence coding for 1) a polypeptide, in particular a ligand, in which one or more amino acids are substituted, inserted or deleted, fused with the cDNA coding for GFP, in particular its mutants S65T or S65C, in which one or more amino acids are substituted, inserted or deleted in order to maintain the reading frame and to obtain a hybrid polypeptide.

The invention also relates to cells containing a DNA sequence coding for a polypeptide, in particular a ligand, in which one or more amino acids are substituted, inserted or deleted, fused with the cDNA coding for GFP, in particular its mutants S65T or S65C, in which one or more amino acids are substituted, inserted or deleted in order to maintain the reading frame, and capable of expressing the DNA sequence considered.

The invention also relates to the culturing of cells containing the ligand-GFP hybrid under conditions allowing
 1) expression of the hybrid polypeptide,
 2) detection of the fluorescence of the cell,
 3) isolation of the ligand-GFP hybrid.

The invention also relates to the incubation of cells expressing the protein-GFP hybrid, in particular a receptor fused with the mutant BFP (GFP Y145F Y66H) with the ligand-GFP hybrid, in particular the mutants S65T or S65C of GFP and measurement of the changes in the fluorescence either of donor (protein-GFP) emission or of acceptor (ligand-GFP) emission, or of acceptor excitation, revealing the protein-ligand interaction, and the addition of a suspected biologically active molecule with the ligand-GFP hybrid and measurement of the adverse changes in the energy transfer signal relative to the incubation of cells expressing the protein-GFP hybrid and the ligand-GFP hybrid.

These various aspects are achieved using a fluorescent protein chosen from fluorescent proteins obtained or derived from autofluorescent proteins of cnidarians, chosen in particular from:
 green fluorescent protein (GFP), or
 variants derived from GFP by addition, deletion or substitution of one or more amino acids, with the proviso that these variants conserve the fluorescence property,
 or fragments of GFP, or fragments of the above-mentioned variants, with the proviso that these fragments conserve the fluorescence property, for the detection and quantification of non-covalent interactions between a target protein labeled with GFP or one of the variants defined above or one of the fragments defined above and one of its ligands labeled with a label consisting:
 either of a molecule which is capable of absorbing the light emitted by the fluorescent protein,
 or of a fluorescent substance, this detection and quantification taking place by fluorescence energy transfer:
 between GFP or one of the variants defined above, or one of the fragments defined above, and the above-mentioned fluorescent substance, the fluorescent substance being such that either it is excitable at the emission wavelength of GFP or of one of the above-mentioned variants, or of one of the above-mentioned fragments, or it emits at the excitation wavelength of GFP, or of one of the above-mentioned variants, or of one of the above-mentioned fragments, or
 between GFP or one of its variants defined above, or one of the fragments defined above, and the above-mentioned molecule which is capable of absorbing the light emitted by the fluorescent protein.

The invention consists in detecting non-covalent interactions between a protein and one of its ligands, by fluorescence energy transfer, and in using this process to screen biologically active molecules, in particular in the field of receptors. The protein is made fluorescent by fusing its cDNA with the cDNA coding for GFP; the ligand is made fluorescent either by chemical grafting of a fluorescent group or by fusion of its gene with that of GFP. The interaction between the protein and its ligand entails changes in the fluorescence spectrum of GFP and/or of the ligand which can be recorded in real-time or at equilibrium.

The non-covalent interaction between a target protein and its ligand corresponds to the formation of a complex between the target protein and the ligand, in which the target protein and the ligand interact with each other, and are found intact after suppression of the interaction.

A series of tests allowing determination of the specific and saturable non-covalent nature of the interaction is described in particular in the following articles: Levitski, A. 1980, in Cellular receptors for hormones and neurotransmitters, Eds Schulster, D. & Levitski, A., John Wiley & Sons Ltd.; Horovitz, H. and Levitski, A. 1987, Proc. Natl. Acad. Sci. 84:6654–6658; Receptor Biochemistry and Methodology, volume 3, Ventre, J. C. & Harrison, L. C. Eds, Alan R. Liss, INC, New York, 1987.

In the present context, the following terms are thus defined:
 autofluorescent protein: synthetic or natural protein in which the chromophore is formed by an autocatalytic reaction between amino acids of the protein without requiring the addition of a prosthetic group and whose fluorescence properties are intrinsic to the monomer,
 "hybrid polypeptide": indicates a polypeptide which is a fusion of at least a part of two proteins, in the invention, by way of example, at least a part of GFP with a part of a target protein or a part of a polypeptide ligand of the target protein,
 "competitor": any molecule which binds to the target protein at the same site as the fluorescent ligand,
 "biologically active substance": any substance capable of interfering with the interaction of a fluorescence ligand and of the specific fluorescent protein, modifying the kinetic or thermodynamic parameters of the interaction.

The expression "fluorescence energy transfer" corresponds to a physical, distance-dependent process, through which the energy is transmitted in a non-radiative manner from an excited chromophore, the donor, to another chromophore, the acceptor, by dipole—dipole interaction (Förster 1951 in Fluoreszenz organischer Verbindung [Fluorescence of Organic Compounds] Vandenhoek and Rupprecht, Göttingen; Wu and Brand 1994 Anal. Biochem. 218:1–13; Clegg 1995, Current Opinion in Biotechnol. 6:103–110). The energy transfer can be observed either by reducing the amplitude of the donor's emission or by increasing the amplitude of the acceptor's excitation and emission.

In the case of the application of energy transfer to biological samples in non-covalent interaction, the transfer signal cannot persist if the experimental conditions do not allow the interaction between the fluorescent ligand and the fluorescent target protein. Similarly, if one of the two partners interacting is not fluorescent, the possible fluorescence variations observed for the other partner cannot be attributed to an energy transfer process.

The terms "change" or "variation" in fluorescence, defined in the context of the energy transfer, refer to any modification of 1) the amplitude of the donor's fluorescence signal, 2) the amplitude of the excitation spectrum or 3) the amplitude of the donor's emission signal. Variations or changes in fluorescence should not be observed if one of the two partners is not fluorescent or if the interaction between the fluorescent partners is inhibited, for example with an excess of a competitive agent.

More specifically, the fluorescence energy transfer reaction requires two fluorescent groups, one referred to as the donor and the other the acceptor. This reaction takes place when two conditions are met:

1) the acceptor's absorption spectrum and the donor's emission spectrum must overlap at least partially; the overlapping is calculated from experimental data and from an equation giving a value in $cm^3 M^{-1}$ (Lakey et al. 1991, J. Mol. Biol. 218:639–653);

2) the donor and the acceptor must be close in space (from 10 to 100 angstroms) in order for the energy transfer to be able to take place.

A consequence of the first condition is that the excitation of the donor then entails a concomitant reduction in the amplitude of the donor's emission and the appearance of an emission signal from the acceptor. This makes it possible to detect the interactions between the donor and the acceptor and/or to measure their distance.

The expression "close in space" means that the distance between the donor and the acceptor is less than or equal to 2 Ro, Ro representing the Forster beam (op.cit.) (Lakey, J. H. et al. 1991, J. Mol. Biol. 218:639–653).

If the acceptor is not fluorescent, but has an excitation spectrum which at least partially overlaps the donor's emission spectrum, the energy transfer may be detected in the form of a reduction in the amplitude of the donor's emission.

The invention relates to the use of a ligand labeled with a label consisting:
  either of a molecule which is capable of absorbing the light emitted by the fluorescent protein,
  or of a fluorescent substance, for the detection and quantification of non-covalent interactions between a target protein and the above-mentioned ligand, the said target protein being labeled genetically with a fluorescent protein chosen from fluorescent proteins obtained or derived from autofluorescent proteins of cnidarians, the molar extinction coefficient of which is greater than about 14,000 $M^{-1}$ $cm^{-1}$ and the quantic fluorescence yield is greater than about 0.38, this protein being chosen in particular from:
  green fluorescent protein (GFP), or
  variants derived from GFP by addition, deletion or substitution of one or more amino acids, with the proviso that these variants conserve the fluorescence property,
  or fragments of GFP, or fragments of the above-mentioned variants, with the proviso that these fragments conserve the fluorescence property, this detection and quantification taking place by fluorescence energy transfer:

between GFP or one of the variants defined above, or one of the fragments defined above, and the above-mentioned fluorescent substance, the fluorescent substance being such that either it is excitable at the emission wavelength of GFP or of one of the above-mentioned variants, or of one of the above-mentioned fragments, or it emits at the excitation wavelength of GFP, or of one of the above-mentioned variants, or of one of the above-mentioned fragments, or between GFP or one of its variants defined above, or one of the fragments defined above, and the above-mentioned molecule capable of absorbing the light emitted by the fluorescent protein.

According to one advantageous embodiment, the fluorescent protein is chosen from:
  green fluorescent protein (GFP) (Ward et al. 1980, Photochem. Photobiol. 31:611–615; Chalfie 1995, Photochem. Photobiol. 62:651–656),
  cyan fluorescent protein (CFP) (Heim & Tsien, Current Biology, 1996, vol. No. 6, pp. 178–182),
  yellow fluorescent protein (RSGFP or EGFP) (Cormack et al. 1995, Gene 173:33–38; Heim, Cubitt and Tsien 1995, Nature; Ehrig et al. 1995, FEBS Lett. 367: 163–166),
  GFPUV (Crameri et al. 1996, Nature Biotechnol. 14:315–319; Ehrig et al. 1995, FEBS Lett. 367:163–166),
  or mutants thereof in which the codons are optimized for expression in human, bacterial or plant cells.

The expression "optimized codons" indicates the replacement of codons of the wild-type protein with the host organism's preferred homologies thereof, without changing the code and thus without changing the protein sequence.

The wild-type (WT) GFP with excitation and emission wavelengths of 395/470–509 is described in the references: Ward et al. 1980 Photochem. Photobiol. 31:611–615, Chalfie 1995, Photochem. Photobiol. 62:651–656.

The GFPUV exhibiting the following mutations: F99S, M153T, V163A with excitation and emission wavelengths of 395 and 510, respectively, is described in Crameri et al. 1996 Nature Biotechnol. 14:315–319, or with the mutation T203I and the excitation and emission wavelengths of 400 and 512, respectively, is described in Ehrig et al. 1995 FEBS Lett. 367:163–166.

The RSGFP (S65T and S65C mutations) with excitation and emission wavelengths of 490 and 510, respectively, is described in Heim, Cubitt and Tsien, Nature 1995, 373: 663–664, or with the E222G mutation and with excitation and emission wavelengths of 480 and 506, respectively, is described in Ehrig et al. 1995 FEBS Lett. 367:163–166.

The EGFP (F64L and S65T mutations) with excitation and emission wavelengths of 490 and 510, respectively, is described in Cormack et al. 1995 Gene, 173:33–38.

The BFP (Y145F and Y66H mutations) with excitation and emission wavelengths of 381 and 448, respectively, is described in Current Biology 1996, 6:178–182.

The various GFP mutants can also be optimized (by the introduction of silent mutations which optimize the use of codons specific to each species) for expression in the following cells:
  human: ref. Haas et al. 1996 Curr. Biol. 6:315–323; Yan et al. 1996, Nucleic Ac. Res. 24:4592–4593; Zolotukhin et al. 1996, J. Virol. 70:4646–4654
  bacterial: Crameri et al. 1996 Nature Biotechnol. 14:315–319, Cormack et al. 1996, Gene, 173:33–38 for *Escherichia coli*, plant: Reichel et al. 1996, Proc. Natl. Acad. Sci. 93:5888–5893.

GFP:

The term GFP indicates a protein coded for by the nucleotide sequence given in FIG. 1, and which emits a fluorescence once it is expressed in cells. GFPs with substitutions, additions or deletions of amino acids which have an influence either on the fluorescence properties or on the degree of expression of the GFP are referred to as GFP mutants.

The invention also relates to the use of a fluorescent protein (No 1) as defined above, in which the ligand is labeled either with a fluorescent substance, the labeling being carried out:

either via a chemical route, the fluorescent substance then being a chemical compound, or or via a recombinant route, the fluorescent substance then being a fluorescent peptide or protein (No 2) which can be chosen in particular from the fluorescent proteins obtained or derived from autofluorescent proteins of cnidarians, this fluorescent substance being chosen in particular from:

green fluorescent protein (GFP), or variants derived from GFP by addition, deletion or substitution of one or more amino acids, with the proviso that these variants conserve the fluorescence property, or fragments of GFP, or fragments of the above-mentioned variants, with the proviso that these fragments conserve the fluorescence property, or with a non-fluorescent substance belonging to the Acid Violet group [Acid Violet 5, CAS 10130-48-0; Acid Violet 7, CAS 4321-69-1; Acid Violet 17, CAS 4129-84-4], the Acid Red group [Acid Red 1, CAS 3734-67-6; Acid Red 8, CAS 4787-93-3; Acid Red 37, CAS 6360-07-2; Acid Red 40, CAS 12167-45-2; Acid Red 106, CAS 6844-74-2; Acid Red 114, CAS 6459-94-5], alizarins, aluminon, azocarmine B [CAS 25360-72-9], basic fuschin [Basic Red 9, CAS 569-61-9], Bordeaux R [Acid Red 17, CAS 5858-33-3] and Carmine [CAS 1390-65-4].

"CAS" corresponds to Chemical Abstracts.

Labeling:

the "labeling" of a target protein or of a ligand means:

for the target protein, the fusion of its gene or cDNA, or part of the gene or cDNA, with the gene or cDNA, or part of the gene or cDNA, of GFP;

for the ligand, it can be a chemical coupling between the ligand and a fluorescent group, or else the fusion of its gene or cDNA, or part of the gene or cDNA, with the gene or cDNA, or part of the gene or cDNA, of GFP.

The invention relates to the use of a fluorescent protein wherein the target protein is labeled with the YP or EGFP protein and the ligand is labeled with the BFP protein, or the target protein is labeled with the BFP protein and the ligand is labeled with the YP or EGFP protein.

The invention also relates to the use of a fluorescent protein chosen from the fluorescent proteins obtained or derived from the autofluorescent proteins of cnidarians, this protein being chosen in particular from:

green fluorescent protein (GFP), or variants derived from GFP by addition, deletion or substitution of one or more amino acids, with the proviso that these variants conserve the fluorescence property, or fragments of GFP, or fragments of the above-mentioned variants, with the proviso that these fragments conserve the fluorescence property, for the detection and quantification of non-covalent interactions between a target protein labeled with GFP or one of the variants defined above or one of the fragments defined above and one of its ligands labeled with a fluorescent substance, this detection and quantification taking place by fluorescence energy transfer between GFP or one of the variants defined above, or one of the fragments defined above, and the said fluorescent substance, the fluorescent substance being such that either it is excitable at the emission wavelength of GFP or of one of the above-mentioned variants, or of one of the above-mentioned fragments, or it emits at the excitation wavelength of GFP, or of one of the above-mentioned variants, or of one of the above-mentioned fragments.

According to one advantageous embodiment of the invention, the fluorescent protein is EGFP and in which:

either the EGFP is a fluorescence energy donor and the label absorbing the light emitted by the EGFP is a fluorescent or non-fluorescent substance, and the marker being chosen from substances whose excitation spectrum overlaps the emission spectrum of EGFP, and in particular, when the label is a fluorescent substance, it is chosen from: 4,4-difluoro-4-bora-3a,4a-diaza-s-indacene (Bodipy), eosin, erythrosin, tetramethylrhodamine, sulphorhodamine 101 sold by Molecular Probe under the name Texas Red, and derivatives thereof which, on the one hand, allow grafting, and, on the other hand, have an excitation spectrum which overlaps the emission spectrum of EGFP, and, when the label is not a fluorescent substance, it is chosen from the Acid Violet group [Acid Violet 5, CAS 10130-48-0; Acid Violet 7, CAS 4321-69-1; Acid Violet 17, CAS 4129-84-4], the Acid Red group [Acid Red 1, CAS 3734-67-6; Acid Red 8, CAS 4787-93-3; Acid Red 37, CAS 6360-07-2; Acid Red 40, CAS 12167-45-2; Acid Red 106, CAS 6844-74-2; Acid Red 114, CAS 6459-94-5], alizarins, aluminon, azocarmine B [CAS 25360-72-9], basic fuschin [Basic Red 9, CAS 569-61-9], Bordeaux R [Acid Red 17, CAS 5858-33-3] and Carmine [CAS 1390-65-4], or the EGFP is a fluorescence energy acceptor and the fluorescent substance is a fluorescence energy donor and is chosen from substances whose emission spectrum overlaps the excitation spectrum of EGFP, and in particular from: coumarins, fluorescamine, 6-(N-methylanilino)naphthalene, (mansyl) and derivatives thereof which, on the one hand, allow grafting, and, on the other hand, have an excitation spectrum which overlaps the emission spectrum of EGFP, or the fluorescent protein is BFP and is a fluorescence energy donor and the fluorescent substance is an energy acceptor and is chosen from fluorescein and 7-nitro-2-benzoxa-1,3-diazole.

or the fluorescent protein is BFP and is a fluorescence energy acceptor and the fluorescent substance is an energy donor and is chosen from pyrene and coumarin or derivatives thereof which, on the one hand, allow grafting, and, on the other hand, have an excitation spectrum which overlaps the emission spectrum of BFP.

As regards the target protein, it can be chosen from:

membrane-bound receptors coupled to protein G in particular in Supplement Trends in Pharmacological Sciences, 1997 (*Receptor and ion Channel Nomenclature*), growth factor receptors, in particular those which are structurally linked to the insulin receptor (Yarden, Y. and Ullrich, A. 1988, Biochemistry 27:3113–3119) or to the γ interferon receptor (Brisco, J. et al. 1996, Phylos. Trans. R. Soc. Lond. B. Biol. Sci. 351:167–171; Ihle, J. N. 1995, Nature 377:591–594), ion channel receptors, in particular in Supplement Trends in Pharmacological Sciences, 1997 (*Receptor and ion Channel Nomenclature*), intracellular nuclear receptors, in particular those which are structurally linked to the steroid receptor (Mangelsdorf et al. 1995, Cell, 83:835–839; Wurtz, J. L. et al. 1996, Nature Struct. Biol. 3:206).

According to one advantageous embodiment, the target protein is chosen from membrane-bound receptors coupled to protein G.

In the text hereinabove and hereinbelow, the term "receptor" denotes any molecule of protein nature which can interact non-covalently with a pharmacological agent. Preferably, in the invention, a neurotransmitter, hormone, growth factor, etc. receptor capable of producing, after interaction with a pharmacological ligand, a signal transduction response which can be measured in vivo and/or in vitro.

The expression "signal transduction response" denotes any response, or inhibition of a response, which can be measured in vivo and/or in vitro, resulting from the interaction of a receptor with its specific pharmacological agents and leading to activations or inhibitions of the cell metabolism by acting on the second messengers, enzymes or ion currents.

As regards the signal transduction response for the receptors coupled to the G proteins, the common test consists in determining the activation of the G protein by measuring the binding of GTP (Befort et al. 1996 Neurochem. Res. 11:1301–1307). Other more specific measurements involve, for example, determinations of intracellular concentrations of cAMP, inositol phosphates or calcium, or measurements of the activation of gene transcription or of oncogene activity, depending on the specific type of coupling of the receptor concerned.

For ion channel receptors, the most direct measurements are determinations of ion currents (Hille, B. 1992 in Ion channels of excitable membranes, Sinauer Associates. Sunderlands, Massachussets). Other measurements can, for example, involve determinations of gene transcription or of enzyme activations.

For growth factor receptors, the common tests are those of cell proliferation, differentiation or survival, and often also tests of phosphorylation of specific substrates (Honneger et al. 1988, EMBO J. 7:3053–3060) for each receptor and detection with antibodies specific for phosphoamino acids.

For nuclear receptors, the signal transduction tests are those of gene transcription in which "chromogenic" reporter genes are placed under the control of promoters specific for the transduction routes of the receptor studied.

As examples of membrane-bound receptors coupled to G proteins, mention may be made of the receptors of purines and nucleotides, biogenic amines of proteins and peptides, eicosanoids, lipids and derivatives, excitatory amino acids and ions, olfactory molecules, as well as orphan receptors (a fairly exhaustive list is given below).

Examples of growth factor receptors which may be mentioned are cytokines, epidermal growth factor, insulin, growth factor derived from platelets, and transforming growth factor.

Ion channel receptors which may be mentioned in particular are the ATP, serotonin, GABA, glycine, acetylcholine and glutamate receptors.

Examples of nuclear receptors which may be mentioned in particular are the thyroid hormone, oestrogen, glucocorticoid and retinoid receptors.

As ligands of receptors coupled to protein G, mention may be made of:

Purines and Nucleotides
  Adenosine
  cAMP
  ATP
  UTP
  ADP
Biogenic Amines (and connected natural ligands)
  5-Hydroxytryptamine
  Acetylcholine
  Dopamine
  Adrenalin
  Histamine
  Melatonin
  Noradrenalin
  Tyramine/Octopamine
  other connected compounds
Peptides
  Adrenocorticotrophic hormone (ACTH)
  Melanocyte stimulating hormone (MSH)
  Melanocortins
  Neurotensin (NT)
  Bombesin and related peptides
  Endothelins
  Cholecystokinin
  Gastrin
  Neurokinin B (NKB)
  Tachykinin receptor
  Substance K (NKA)
  Substance P (SP)
  Neuropeptide Y (NPY)
  Thyrotropin releasing factor
  Nociceptin
  Bradykinin
  Angiotensin II
  Beta-endorphin
  C5a anaphalatoxin
  Calcitonin
  Chemokines (also known as intercrines)
  Corticotrophin releasing factor (CRF)
  Dynorphin
  Endorphin
  Formylated peptides
  Follitropin (FSH)
  Pheromones of fungal maturation
  Galanin
  Receptor of gastric inhibitor polypeptide (GIP)
  Glucagon-like peptides (GLPs)
  Glucagon
  Gonadotropin-releasing hormone (GmRH)
  Growth factor releasing hormone (GHRM)
  Insect diuretic hormone
  Interleukin
  Leutropin (LH/HCG)
  MET-encephalin
  Opioid peptides
  Oxytocin
  Parathyroid hormone (PTH) and (PTHrP)
  Peptides activating pituitary adenyl cyclase (PACAP)
  Secretin Somatostatin
Thrombin
Thyrotropin (TSH)
Vasoactive intestinal peptide (VIP)
Vasopressin
Vasotocin
Eicosanoids
  IP-Prostacyclins
  PG-Prostaglandins
  TX-Thromboxanes
Retinal-based compounds
  Vertebrate 11-cis retinal
  Invertebrate 11-cis retinal
Lipids and lipid-based compounds
  Cannabinoids
  Anandamide
  Lysophosphatidic acid
  Platelet activating factor
  Leukotrienes
Excitatory amino acids and ions
  Calcium ion
  Glutamate
Orphan Receptors
  Olfactory receptors The ligand can be either an agonist or an antagonist.

The term "agonist" means any molecule which mimics the effect of the natural endogenous ligand, for example the neurotransmitter, the growth factor or the hormone.

The term "antagonist" refers to any molecule which inhibits the effect of the agonist by binding to the same target protein as this agonist.

The invention relates to a process for detecting and quantifying non-covalent interactions between a target protein, in particular a receptor, and one of its ligands, characterized in that:

cells or cell fragments are prepared containing a DNA sequence comprising the gene coding for a fluorescent protein fused with the gene for the target protein, the fusion between the gene for the fluorescent protein and the gene for the above-mentioned target protein being such that the properties of the target protein, in particular of the receptor, are not modified by the presence of the fluorescent protein, namely:
    the interaction between the target protein, in particular the receptor, and the ligand is not modified,
    the response transduction function is not modified, the fluorescent protein being chosen from the fluorescent proteins obtained or derived from autofluorescent proteins of cnidarians, this protein being chosen in particular from:
      green fluorescent protein (GFP), or
      variants derived from GFP by addition, deletion or substitution of one or more amino acids, with the proviso that these variants conserve the fluorescence property,
      or fragments of GFP, or fragments of the above-mentioned variants, with the proviso that these fragments conserve the fluorescence property,
  the above-mentioned cells or the above-mentioned cell fragments are placed in contact with a ligand for the above-mentioned target protein, in particular for the above-mentioned receptor, labeled with a label consisting:
    either of a molecule capable of absorbing the light emitted by the fluorescent protein,
    or of a fluorescent substance,
  and either the fluorescent protein being the fluorescence energy donor and the label being the fluorescence energy acceptor, or the fluorescent protein being the fluorescence energy acceptor and the label being a fluorescent substance which is a fluorescence energy donor, and
    irradiation is carried out at a wavelength which makes it possible either to excite the fluorescent protein or to excite the fluorescent substance,
    it being possible for the above-mentioned steps of placing in contact and irradiation to be carried out either simultaneously or one after the other, or
  the above-mentioned cells or the above-mentioned cell fragments are placed in contact with a ligand for the above-mentioned protein, in particular for the above-mentioned receptor, labeled with a label, the cells or the ligand having been irradiated before being placed in contact,
    either a reduction in the amplitude of the donor's emission and/or an emission signal characteristic of the acceptor's emission is detected.

Cells, fragments and purified protein:

The term "cell" means any eukaryotic or prokaryotic, animal or plant cell in which the gene coding for the fusion protein is introduced between the receptor (described) and GFP or its mutants or fragments.

The expression "cell fragment" means any fraction, which may or may not be membrane-bound, obtained from cells and containing the receptor-GFP fusion protein.

The expression "purified protein" means a partially or totally purified fusion protein.

According to one advantageous embodiment, the process uses for cDNA of the EGFP variant of green fluorescent protein fused to a receptor in combination with a ligand for the said receptor labeled with Bodipy 530–550. The preferred expression system is the mammalian or yeast cell.

The invention also relates to a process for detecting and quantifying non-covalent interactions between a target protein, in particular a receptor, and one of its ligands, characterized in that:

a fluorescent protein fused with a target protein, the protein-ligand interaction of which it is desired to determine, is prepared, the fusion between the fluorescent protein and the above-mentioned target protein being such that the properties of the protein, in particular of the receptor, are not modified by the presence of the fluorescent protein, namely:
    the interaction between the target protein, in particular the receptor, and the ligand is not modified,
    the response transduction function is not modified,
    the fluorescent protein being chosen from the fluorescent proteins obtained or derived from autofluorescent proteins of cnidarians, this protein being chosen in particular from:
      green fluorescent protein (GFP), or
      variants derived from GFP by addition, deletion or substitution of one or more amino acids, with the proviso that these variants conserve the fluorescence property,
      or fragments of GFP, or fragments of the above-mentioned variants, with the proviso that these fragments conserve the fluorescence property,
  the above-mentioned fluorescent protein fused with the target protein is placed in contact with a ligand for the above-mentioned protein, in particular for the above-mentioned receptor, this ligand being labeled with a label consisting:

either of a molecule which is capable of absorbing the light emitted by the fluorescent protein,
or of a fluorescent substance,
and either the fluorescent protein being a fluorescence energy donor and the label being a fluorescence energy acceptor, or the fluorescent protein being a fluorescence energy acceptor and the label being a fluorescent substance which is a fluorescence energy donor, and
irradiation is carried out at a wavelength which makes it possible either to excite the fluorescent protein or to excite the fluorescent substance,
it being possible for the above-mentioned steps of placing in contact and irradiation to be carried out either simultaneously or one after the other, or
the above-mentioned fluorescent protein fused with the target protein is placed in contact with a ligand for the above-mentioned protein, in particular for the above-mentioned receptor, this ligand being labeled with a label consisting:
either of a molecule which is capable of absorbing the light emitted by the fluorescent protein,
or of a fluorescent substance,
the fluorescent protein fused with the target protein or the ligand having been irradiated before being placed in contact, either a reduction in the amplitude of the donor's emission and/or an emission signal characteristic of the acceptor's emission is detected.

In addition to exhibiting the fluorescence of GFP, the target protein, and in particular the receptor modified by fusion with GFP, will have to conserve pharmacological properties which are compatible with its definition as a receptor specific for the compounds characterizing it. In particular, it will have to be able to bind the same ligands as the wild-type receptor.

In the process of the invention, the placing in contact of the fluorescent protein fused with the target protein and the ligand, or of cells or cell fragments (containing the above-mentioned fluorescent protein fused with the target protein) and the ligand, leads to a mixture.

The mixing can be carried out in any order of addition. The preferred order will be the addition of fluorescent ligand to a solution of cells or protein, if GFP is the donor, and the reverse if GFP is the acceptor.

The mixing can be carried out in a device for rapid mixing combined with a system for detecting fluorescence in order to gain access to real-time measurements of the receptor-ligand interaction and of its impairments by biologically active molecules.

Introduction of DNA into the cells:

The animal, plant, insect, yeast, bacterial or fungal cells constituting the expression system chosen may be either transfected, transformed, electroporated or infected, in a stable or transient manner, according to the protocols described in the laboratory manuals, for example Current Protocols in Molecular Biology, eds Ausabel et al., John Wiley and sons.

The invention also relates to a process in which the fluorescent protein is EGFP and in which:
either the EGFP is a fluorescence energy donor and the label is a fluorescence energy acceptor and is chosen from substances whose excitation spectrum overlaps the emission spectrum of EGFP, and in particular, when the label is a fluorescent substance, it is chosen from: 4,4-difluoro-4-bora-3a,4a-diaza-s-indacene (Bodipy), eosin, erytlirosin, tetramethylrhodamine, sulphorhodanine 101 sold by Molecular Probe under the name Texas Red, and derivatives thereof which, on the one hand, allow grafting, and, on the other hand, have an excitation spectrum which overlaps the emission spectrum of EGFP, and, when the label is not a fluorescent substance, it is chosen from the Acid Violet group [Acid Violet 5, CAS 10130-48-0; Acid Violet 7, CAS 4321-69-1; Acid Violet 17, CAS 4129-84-4], the Acid Red group [Acid Red 1, CAS 3734-67-6; Acid Red 8, CAS 4787-93-3; Acid Red 37, CAS 6360-07-2 Acid Red 40, CAS 12167-45-2; Acid Red 106, CAS 6844-74-2; Acid Red 114, CAS 6459-94-5], alizarins, aluminon, azocarmine B [CAS 25360-72-9], basic fuschin [Basic Red 9, CAS 569-61-9], Bordeaux R [Acid Red 17, CAS 5858-33-3] and Carmine [CAS 1390-65-4], or the EGFP is a fluorescence energy acceptor and the fluorescent substance is a fluorescence energy donor and is chosen from substances whose emission spectrum overlaps the excitation spectrum of EGFP, and in particular from: coumarins, fluorescamine, 6-(N-methylanilino)naphthalene, (mansyl) and derivatives thereof which, on the one hand, allow grafting, and, on the other hand, have an excitation spectrum which overlaps the emission spectrum of EGFP.

The invention also relates to a process in which the protein whose protein-ligand interaction it is desired to determine is chosen from:
membrane-bound proteins coupled to G protein, in particular in Supplement Trends in Pharmacological Sciences, 1997 (*Receptor and ion Channel Nomenclature*),
growth factor receptors, in particular those which are structurally linked to the insulin receptor (Yarden, Y. and Ullrich, A. 1988, Biochemistry 27:3113–3119) or to the γ interferon receptor (Brisco, J. et al. 1996, Phylos. Trans. R. Soc. Lond. B. Biol. Sci. 351:167–171; Ihle, J. N. 1995, Nature 377:591–594),
ion channel-receptors, in particular in Supplement Trends in Pharmacological Sciences, 1997 (*Receptor and ion Channel Nomenclature*),
intracellular nuclear receptors, in particular those which are structurally linked to the steroid receptor (Mangelsdorf et al. 1995, *Cell*, 83:835–839; Wurtz, J. L. et al. 1996, Nature Struct. Biol. 3:206).

The invention also relates to a process in which the fluorescent protein is EGFP and the labeled substance is Bodipy and in which either the reduction in the emission amplitude of EGFP or the emission signal of Bodipy resulting from the energy transfer is detected, the irradiation wavelength corresponding to the excitation wavelength of EGFP.

The invention also relates to a process in which the fluorescent protein is EGFP and the labeled substance is a coumarin and in which either the decrease in the amplitude of coumarin or the emission signal of EGFP resulting from the energy transfer is detected, the irradiation wavelength corresponding to the excitation wavelength of coumarin.

The invention also relates to a process in which the fluorescent protein is fused on the N-terminal side and the target protein, in particular the receptor, is fused on the C-terminal side.

The invention also relates to a process in which the fluorescent protein is fused on the C-terminal side and the target protein, in particular the receptor, is fused on the N-terminal side.

The invention also relates to a process in which the fluorescent protein is inserted into the target protein in a place not corresponding to a target protein-ligand binding site, in particular in the case of receptors coupled to the G protein, this insertion taking place in the first or the third intracellular loop of the receptor, with the proviso that the insertion does not destroy either the properties of the receptor or the fluorescence of the fluorescent protein.

The invention also relates to a process in which the cells are mammalian cells, in particular HEK 293 cells which are adherent or in suspension, CHO cells, COS cells, lymphocytic lines, fibroblasts, etc., or yeast cells, in particular *pichia* such as *pichia pastoris, saccharomyces* such as *saccharomyces cerevisia, saccharomyces kluyveri, Hansenula* such as *Hansenula polymorpha*, or insect cells infected with a virus such as baculovirus, in particular TNI or sf9 cells, or fungi, in particular strains of *Aspergillus* (*A. oryzae, A. nidulans, A. niger*), *Neurospora, Fusarium* or *Trichoderma*.

The use of *Aspergillus* for protein expression is described in EP 0,272,277 or EP 0,230,023 or EP 0,184,438, or cells from plants, in particular *Arabidopsis* (*A. thaliania*), or protoplasts from sweet orange (*Citrus sinensis*) is described in Haseloff, J. and Amos, B. 1995, Trends in Genetics 11:328–329.

As regards the cell line used, this depends on the receptor; specifically, it is desirable to choose a line which does not already naturally express the receptor chosen.

The invention also relates to a process in which a signal can be detected, in a conventional fluorimetry device or in a rapid-mixing device equipped with a system for detecting fluorescence, after mixing the donor and the acceptor, and can be abolished by the addition of a non-fluorescent substance of the same pharmacological specificity, and in particular in which the signal/noise ratio is a greater than about 2.

To establish the ideas and by way of example, the signal/noise ratio is about 100 with the Bodipy-EGFP couple on the equipment used (described in the examples) and with the receptor for the substance which will be denoted as NK2R labeled with EGFP (NK2R-EGFP) and its ligand, substance K (NKA) labeled with Bodipy (NKA-BO).

As regards the signal and the signal-to-noise ratio, it can be defined as follows:

If the mixture of the donor and the acceptor is accompanied by a change in fluorescence, either of the donor or the acceptor, this change must be inhibited and reversed by a non-fluorescent substance (of the same pharmacological specificity) and which moreover defines the specificity of the pharmacological phenomenon observed. For certain applications (response of yes-no type), a low signal-to-noise ratio may suffice.

As regards the target protein, it is possible to take measurements with whole cells (containing the DNA coding for the target protein), cell fragments (membranes for membrane receptors) or samples of target proteins which are dissolved (membrane receptors) or purified (cf. examples).

One subject of the invention is cells or cell fragments containing a DNA sequence comprising the gene coding for a fluorescent protein fused with the gene for a target protein, the fluorescent protein being chosen from the fluorescent proteins obtained or derived from autofluorescent proteins of cnidarians, the fusion between the gene for the fluorescent protein and the gene for the above-mentioned target protein being such that
the properties of the target protein are not modified by the presence of the fluorescent protein, that is to say
the interaction between the target protein and the ligand is not modified,
the response transduction function is not modified, with the proviso that:
when the target protein is the rat glucocorticoid receptor fused at the N-terminal with, successively, a purification sequence comprising 6 histidines, a haemaglutinin epitope and a fluorescent protein and is expressed in the cell line 1471.1 (Htun et al. 1996, PNAS 93:4845–4850), the fluorescent protein is other than GFP (768 base pairs of plasmid TU65 with the mutation S65T) (Chalfie et al. 1994, Science 263:802–805, with the mutation S65T),
when the target protein is the human glucocorticoid receptor truncated of its first 131 amino acids, fused at the C-terminal of a fluorescent protein in the sites Sal I and BamHI and is expressed in the cells Cos-1 (Ogawa et al. 1995, PNAS 92:11899–11903), the said fluorescent protein is other than GFP as described in the article by Inouye S. and Tsuji, F. I., 1994, Febs Letters, 341:277–280,
when the target protein is the rat NMDA R1 sub-unit expressed in HEK 293 cells (according to Marshall et al. 1995, Neuron 14:211–215) fused at the C-terminal with a fluorescent protein, the fluorescent protein is other than that consisting of the amino acids 2–238 of wild-type GFP (Chalfie et al. 1994, Science 263:802–805),
when the target protein is a receptor or a the fragments of a receptor for intracellular second messengers, the fluorescent protein is other than that GFP and its derivatives (WO96/23898).

The invention also relates to a kit or equipment for detecting and quantifying non-covalent interactions between a target protein labeled with a fluorescent protein and one of its ligands labeled with a label consisting:
either of a molecule which is capable of absorbing the light emitted by the fluorescent protein,
or of a fluorescent substance, this fluorescent protein being chosen from the fluorescent proteins obtained or derived from autofluorescent proteins of cnidarians, this protein being chosen in particular from:
green fluorescent protein (GFP), or
variants derived from GFP by addition, deletion or substitution of one or more amino acids, with the proviso that these variants conserve the fluorescence property,
or fragments of GFP, or fragments of the above-mentioned variants, with the proviso that these fragments conserve the fluorescence property and its ligand labeled with a fluorescent substance, the said kit comprising:
the target protein fused with a fluorescent protein or a stable cell line which is capable of expressing the protein fused with a fluorescent protein or a plasmid containing the nucleic acid sequence coding for the said target protein fused with a fluorescent protein as defined above,
the ligand labeled with the above-mentioned label,
the buffers and media required for the energy transfer between the above-mentioned protein and the above-mentioned ligand.

The invention relates to a kit or equipment for detecting and quantifying non-covalent interactions between a target protein labeled with a fluorescent protein (No 1) and one of its ligands labeled with a fluorescent substance corresponding to a fluorescent protein (No 2), the fluorescent protein (No 1) being chosen from the fluorescent protein YP or EGFP and the ligand being labeled with a fluorescent protein (No 2) BFP, or the fluorescent protein (No 1) being BFP and the ligand being labeled with the fluorescent protein (No 2) YP or EGFP, the said kit comprising:

either a plasmid containing a nucleic acid sequence coding for the target protein fused with a fluorescent protein (No 1), and
a plasmid containing a nucleic acid sequence coding for the ligand fused with a fluorescent protein (No 2), or
a ligand fused with a fluorescent protein (No 2), obtained via a recombinant route and purified,
or a stable cell line which is capable of expressing the target protein fused with a fluorescent protein (No 1), and
a stable cell line which is capable of expressing the ligand fused with a fluorescent protein (No 2) or
a ligand fused with a fluorescent protein (No 2), obtained via a recombinant route and purified,
the buffers and media required for the energy transfer between the above-mentioned protein and the above-mentioned ligand.

DETAILED DESCRIPTION OF THE INVENTION

In its preferred embodiment, the development of the invention uses the cDNA coding for green fluorescent protein (Prasher et al. Gene 1992, 111:229–233; GenBank Accession No M62653) from the jellyfish *Aequoria victoria*, preferably the mutants GFPUV, RSGFP and BFP of this fluorescent protein, optimized for their expression in the preferred host organisms, mammalian cells.

The cDNA can be modified to code for a variant in which one or more amino acids are substituted, inserted or deleted in order to allow its N- or C-terminal fusion with the gene coding for a target protein.

The target protein, preferably a receptor, can be chosen from:

1) neurotransmitter receptors coupled to G proteins which are structurally linked to the adrenergic receptors and metabotropic receptors of glutamate, as are given in the annually updated and edited list as a supplement under the name: "Receptor and Ion Chaimel Nomenclature" by Elsevier Trends journals, in Trends in Pharmacological Sciences.

2) the ion receptor-channels which are structurally linked to the nicotinic receptors, to the glutamate receptors and to the ATP receptor, as are given in the annually updated and edited list as a supplement under the name: "Receptor and Ion Channel Nomenclature" by Elsevier Trends journals, in Trends in Pharmacological Sciences.

3) nuclear receptors containing a domain for interaction with DNA which are structurally linked to the steroid receptor (Mangelsdorf et al. 1995, Cell, 83:835–839, Wurtz, J. L. et al. 1996, Nature Struct. Biol. 3:206).

4) plasmid membrane receptors with tyrosine kinase activity, which are structurally linked to the insulin receptor (Yarden, Y. and Ullrich, A. 1988, Biochemistry 27:3113–3119).

5) membrane-bound receptors coupled to the tyrosine kinase proteins (STATs, TYK2, Jak) which are structurally linked to the y interferon receptor (Brisco, J. et al. 1996, Phylos. Trans. R. Soc. Lond. B. Biol. Sci. 351:167–171; Ihle, J. N. 1995, Nature 377:591–594).

When the fusion is carried out between EGFP and a receptor coupled to the G proteins (group 1), the fusion can be carried out in particular:

1) on the N-terminal side of the receptor, and thus on the C-terminal side of EGFP,
2) on the C-termiinal side of the receptor and thus on the N-terminal side of EGFP,
3) in the receptor sequence, in particular in the first or third intracellular loop, optionally by introducing one or more copies of a spacer sequence, in particular -GGGGS-.

When the fusion is carried out between EGFP and a receptor-channel (group 2), the fusion can be carried out in particular:

1) in the region homologous to the "major immunogenic region" of the α sub-unit of the nicotinic receptor of Torpedo (residues 67–76), optionally by introducing one or more copies of a spacer sequence, in particular -GGGGS-.

When the fusion is carried out between EGFP and a nuclear receptor (group 3), the fusion can be carried out in particular:

1) on the N-terminal side of the receptor, and thus on the C-terminal side of EGFP,
2) on the N-terminal side of the receptor, truncated in its N-terminal part upstream of the DNA binding domain, and thus on the C-terminal side of EGFP.

When the fusion is carried out between EGFP and a receptor either with tyrosine kinase activity or coupled to a tyrosine kinase (groups 4 and 5), the fusion can be carried out in particular:

1) on the N-terminal side of the receptor, and thus on the C-terminal side of EGFP, [lacuna]

Any gene coding for a fluorescent protein, in particular GFP, coupled to a receptor, and derived from organisms which express GFP or similar proteins, may be used in this invention.

The DNA sequences coding for GFP and the target proteins, in particular receptors, may be of genomic origin or may be cDNAs, and may be obtained from the DNA of any animal or plant, eukaryotic or prokaryotic species, for example by preparing genome libraries or cDNA libraries and by screening these libraries to identify the coding sequences by hybridization with oligonucleotide probes by the standard techniques (Current Protocols in Molecular Biology, op. cit.).

The DNA constructs coding for GFP and the target proteins can also be obtained by total synthesis by the standard methods, in particular the phosphoramidite method (Beaucage and Caruthers, Tett. Lett. 1981, 22:1859–1869) and the use of automated DNA synthesis devices, the polynucleotide obtained then being purified, ligated and cloned into the appropriate vectors. For most applications, the genes coding for GFP and the target proteins will preferably be obtained by screening libraries, while the spacer arms and the oligonucleotides required for the mutagenesis will preferably be obtained by synthesis.

The DNA constructs may be of mixed, synthetic and genomic nature, by ligation of synthetic fragments with genomic DNA elements, according to standard procedures (Current Protocols in Molecular Biology, op. Cit.).

The DNA constructs can also be obtained by PCR (polymerase chain reaction) using specific primers, for example as described in PCR protocol 1990, Academic Press, San Diego, Calif., USA.

Finally, the DNA constructs can be modified by other methods including, for example, chemical reactions, random or site-directed mutagenesis, by insertion, deletion or substitution of nucleotides, it being possible for these modifications to adversely affect the properties of one or other protein, in particular GFP and the targets proteins.

The DNA constructs can be inserted into a recombinant vector. This vector may be any vector which is suitable for the procedures used with recombinant vectors. The choice of vector will often be made as a function of the host cell into which it will be desired to introduce the DNA construct. The vector may thus be a vector capable of replicating autonomously, that is to say extra-chromosomally, and independently of the chromosomal replication, for example a plasmid. Alternatively, the vector may be developed so as to incorporate or some of the DNA it contains into the genome of the host cell, and will replicate at the same time as the chromosome(s) into which it will be incorporated.

The vector is preferably an expression vector in which the GFP fused with the target protein or the GFP fused with the ligand is under the control of other segments of DNA required for the transcription. In general, the expression vector is derived from viral or plasmid DNA or can contain elements of one and the other.

The expression "under the control" indicates that the DNA segments are arranged on the vector so as to function in concert in order to serve the desired objective; for example, the transcription is initiated in the promoter and continues throughout the sequence coding for the target protein fused with GFP or the ligand fused with GFP.

The promoter can be any DNA sequence which is capable of promoting a transcriptional activity in the host cell chosen and can be derived from gene which are homologous or heterologous with the host cell.

Examples of promoters which are suitable for expressing the target protein fused with GFP or the ligand fused with GFP in mammalian cells are the simian virus SV40 promoter (Subramani et al. 1981, Mol Cell. Biol. 1:854–864), the Rous sarcoma virus (RSV) promoter, the cytomegalovirus (CMV) promoter or the adenovirus major late promoter (AdMLP).

Examples of Promoters for Insect Cells:

Polyhedrin promoter (U.S. Pat. No. 4,745,051; Vasuvedan et al. 1992., FEBS Lett. 311:7–11) the promoter P10 (Vlack et al. 1988, J. Gen. Virol. 69:765–776) the promoter for the early gene 1 of baculovirus (U.S. Pat. No. 5,155,037; U.S. Pat. No. 5,162,222).

Examples of Promoters for Yeasts:

Promoters of the glycolysis genes (Hitzeman et al. J. Biol. Chem. 1980, 255:12073–12080; Alber and Kawasaki, J. Mol. Appl. Gen. 1982, 1:419–434) of alcohol dehydrogenase genes (Young et al. in Genetic Engineering of microorganisms for chemicals (Hollaender et al. eds), Plenum Press, NY 1982).

Examples of Promoters for Bacteria:

Examples of promoters for expression in bacteria can be constitutive promoters such as the T7 polymerase promoter, or inducible promoters such as, for example, the pL promoter of the lambda phage (Current Protocols in Molecular Biology, op.cit.).

Examples of Promoters for Filamentous Fungi

The promoters which can be used are, for example, the ADH3 promoter (McKnight et al. EMBO J. 1985, 4:2093–2099) or the tpiA promoter. Other useful promoters may be derived from genes coding for the aspartate proteinase of *Rhizomucor miehei*, neutral alpha-amylase of *Aspergillus niger*, acetamidase of *Aspergillus nidulans*, TAKA amylase of *Aspergillus oryzae* or the glucoamylase promoter of *Aspergillus awamori*.

The vector may moreover contain:

polyadenylation sequences such as, for example, those of SV40 or of the Elb 5 region of adenovirus, transcription activator (enhancer) sequences (the SV40 activator), replication sequences such as, for example, the sequences for replication of SV40 or of Epstein Barr virus, for mammalian cells, or at the origin and replication genes REP 1–3 of the plasmid 2μ, for yeasts, selection markers, i.e. genes which impart resistance to an antibiotic (neomycin, zeocin, hygromycin, ampicillin, kanainycin, tetracyclin, chloramphenicol, etc.) or which allow for the compensation of a defect (gene coding for dihydrofolate reductase allowing resistance to methotrexate, or the TPI gene of *S. pombe* described by Russell, 1985, Gene, 40:125–130).

The host cell can be any cell capable of expressing the DNA construct inserted into a suitable vector.

The cells can be, in particular, bacteria, yeasts, fungi and higher eukaryotic cells such as, for example, mammalian cells.

Examples of Bacterial Cells which are Capable of Expressing the DNA Constructs are:

gram-positive bacteria such as *Bacillus* strains, for instance *B. subtilis, B. licheniformis, B. lentus, B. brevis, B. strearothermophilus, B. thurigiensis* or *Streptomyces* strains, for instance *S. lividans, S murinus*, grain-negative bacteria such as *Escherichia coli*.

Transformation of the bacteria can be carried out by protoplastic transformation or by transformation of competent bacteria (Current Protocols in Molecular Biology, op.cit.).

Examples of Eukaryotic Cells:

Cell lines HEK 293, HeLa, primary cultures, COS cells (e.g. ATCC CRL 1650), BHK (e.g. ATCC CRL 1632) CHO (e.g. ATCC CCL 61).

The methods for introducing DNA into these cells (transfection, lipofection, electroporation etc., are described in Current Protocols in Molecular Biology, op.cit.

Examples of Yeast Cells:

*Saccharomyces, S. cerevisiae, S. kluyveri,*

*Kluiveronmyces, K lactis,*

*Hansenula, H polymorpha,*

*Pichia, P. pastoris,* transformed by introduction of heterologous DNA according to the protocols described in Current Protocols in Molecular Biology, op.cit.

The transformed cells are selected by a phenotype determined by a resistance marker, generally a marker of resistance to a drug, or by their capacity to proliferate in the absence of a particular nutrient Examples of Filamentous Fungi:

The strains *Aspergillus* (*A. oryzae, A. nidulans, A. niger*), *Neurospora, Fusarium, Trichoderma*. The use of *Aspergillus* for the expression of proteins is described in EP 272 277 or EP 230 023 or EP 184 438.

Examples of Insect Cells:

Mention may be made of *Lepidoptera* lines e.g. *Spodoptera frugiperda* (Sf9) or *Trichoplusia ni* (Tni). The transformation methods (in particular infection) are described in Current Protocols in Molecular Biology (op.cit.).

The Ligands

The ligands which interact with the target protein can be of any origin (natural, synthetic, semi-synthetic or recombinant) and of any structure (chemical, peptide or protein). They can be naturally fluorescent (or a bearing a chromophore) or can either require a chemical reaction for grafting a fluorescent group (or a precursor of a fluorescent group) or a chromophore, or require a DNA construct leading to fusion of the ligand with GFP and allowing the expression of the ligand thus made fluorescent.

Examples of Chemical Reactions are:
the coupling of amines or thiols with reagents such as alkyl halides, aryl halides, acyl halides, acid halides, the isothiocyanate group, the maleimide group or epoxides, in an organic solvent in the presence of a base or in aqueous medium,
coupling of acids with amines activated with groups such as succinimides.

According to the process of the invention, the fluorescence of the transformed cells can be measured in a spectrofluorimeter with the aid of which the spectral properties of the cells, in suspension or adherent, can be determined by acquisition of their excitation and emission spectra. The interactions with the fluorescent ligand are then detected by means of the changes in the donor's and acceptor's excitation and/or emission energy spectra, and the ligands are defined as being pharmacologically significant if their interactions with the target protein are inhibited by the addition of an excess of non-fluorescent ligand which prevents the interaction between the fluorescent target protein and the fluorescent ligand.

DESCRIPTION OF THE FIGURES

Figure 1:
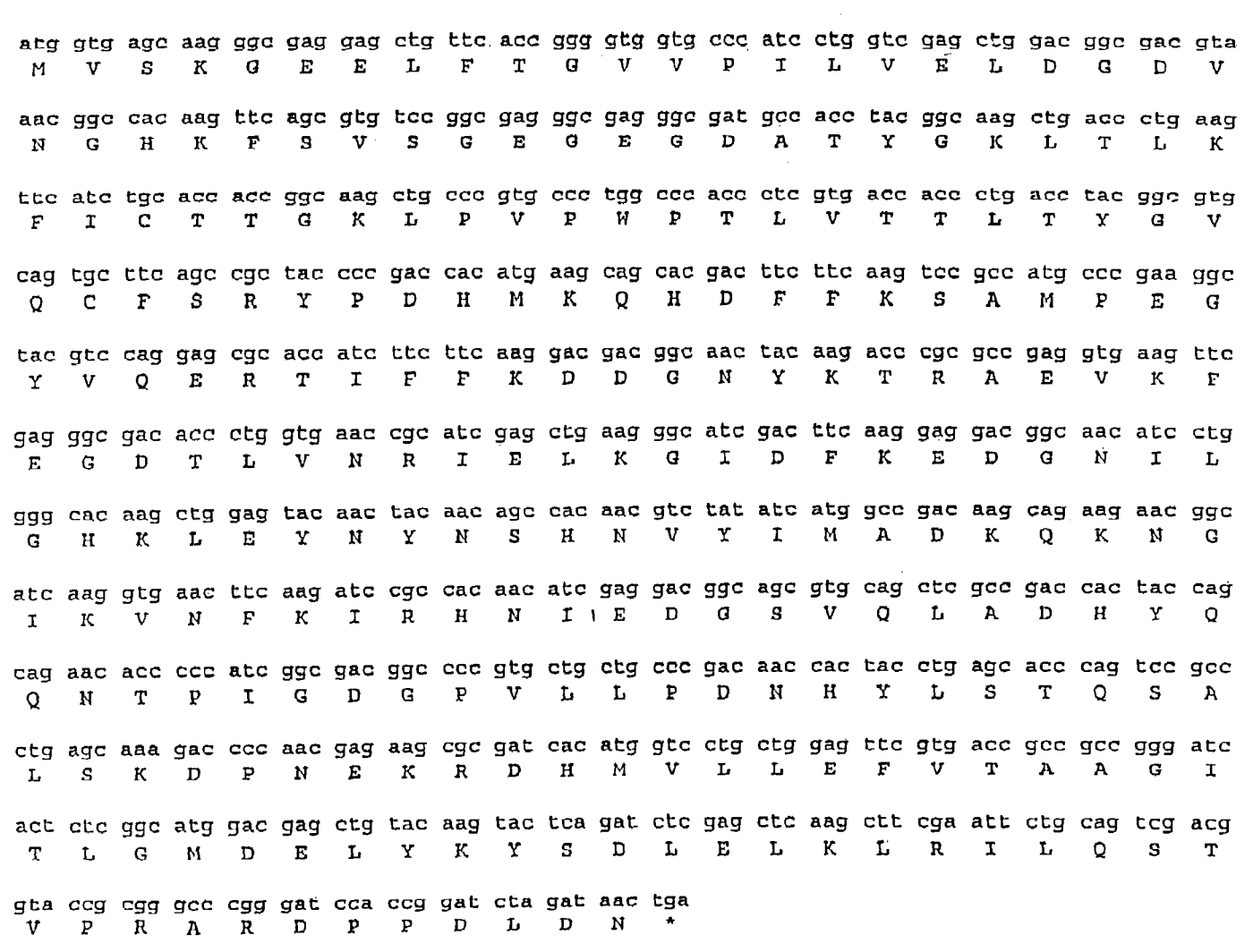

FIG. 1 gives the nucleotide sequence coding for the wild-type GFP (Prasher et al. 1992, Gene 111:229–233) of *Aequorea victoria*.

The broken curves represent the excitation spectra (emission at 540 nm) of pCEP4-NK2R (narrow lines) and pCEP4-NK2R-RF1 (thick lines).

The solid lines represent the emission spectra (excitation at 450 nm) of pCEP4-NK2R (narrow lines) and pCEP4-NK2R-RF1 (thick lines).

Figure 4A:
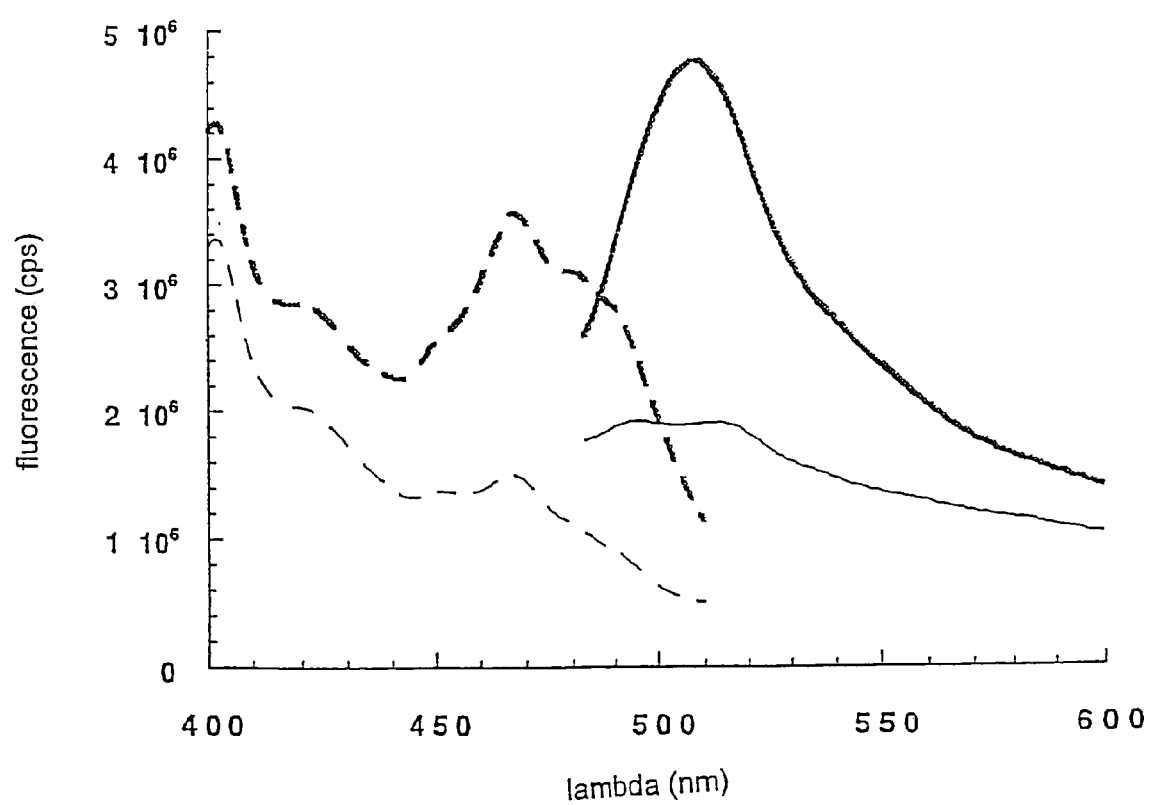
FIG. 4a represents the excitation spectrum (emission at 540 nm) and the emission spectrum (excitation at 450 nm) of HEK 293 cells in suspension, expressing the DNA constructs pCEP4-NK2R and pCEP4-NK2R-RF1. The fluorescence expressed in counts per second (cps) is given on the y-axis and the emission wavelength is given on the x-axis.
Figure 4B:
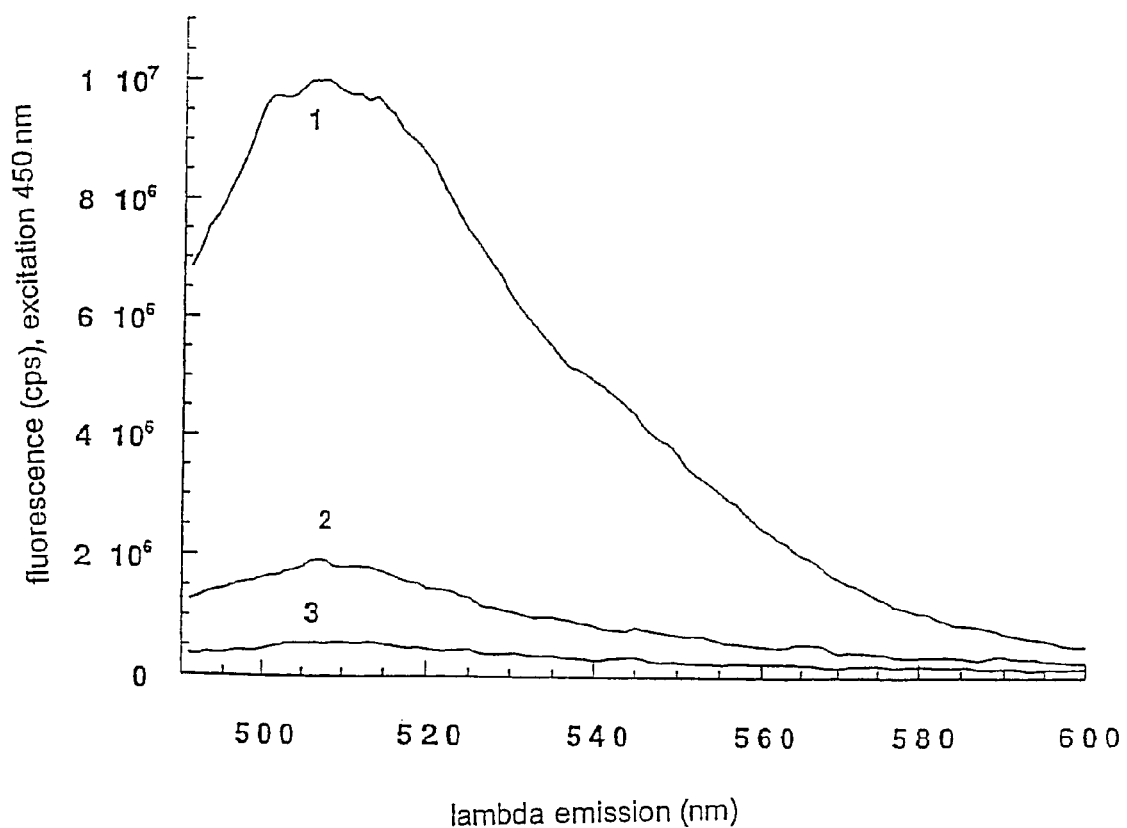

FIG. 4b represents the emission spectrum (excitation at 450 nm) of cells expressing the receptors NK2R-WT (curve No 3), NK2R-RF1 (curve No 1) and NK2R-RF2 (curve No 2). The fluorescence expressed in counts per second (cps) is given on the y-axis and the emission wavelength is given on the x-axis.

Figure 5A:
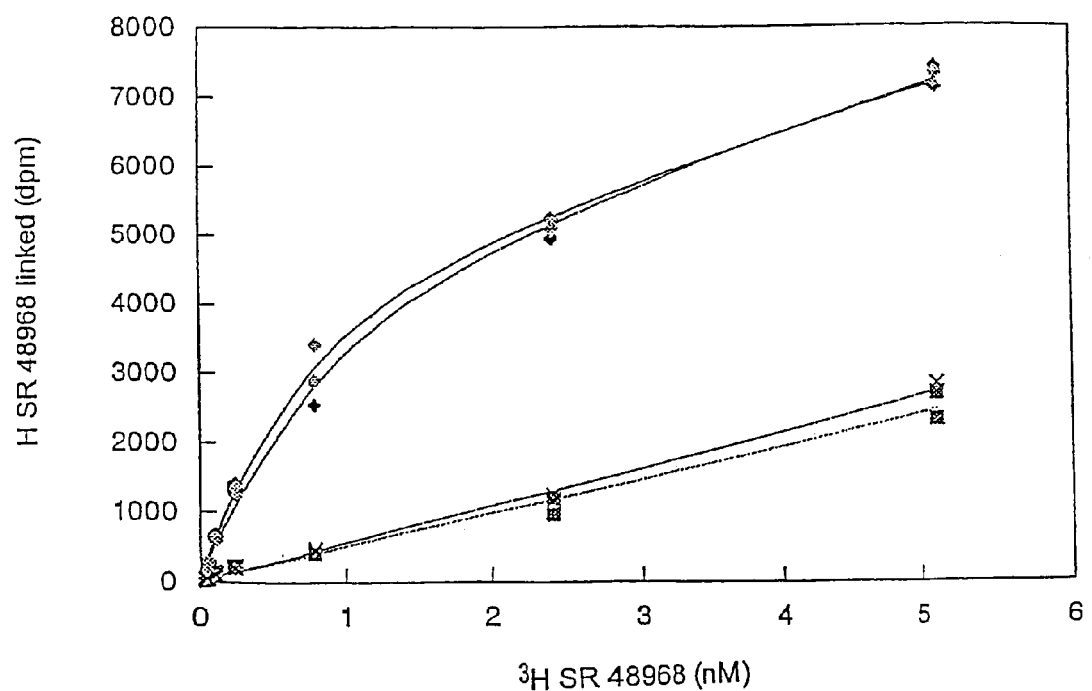

FIG. 5a represents the binding of the antagonist $^3$H SR 48968 to cells expressing the wild-type NK2R receptor. The amount of bound $^3$H SR 48968 is given on the y-axis (in disintegrations per minute; dpm) and the concentration of $^3$H SR 48968 added to the sample is given on the x-axis. The gray and black diamonds represent the total binding of $^3$H SR 48968 in two different experiments, and the gray crosses and squares represent the non-specific binding determined in the presence of an excess of neurokinin A (10 μM). The lines correspond to the theoretical curves for the binding of a ligand to its receptor or to non-specific binding sites. The affinity values determined (KD) are 1.05 nM and 0.78 nM in each of the two experiments. The maximum binding values (13 max) are both 0.1 pMol/25,000 cells.

Figure 5B:
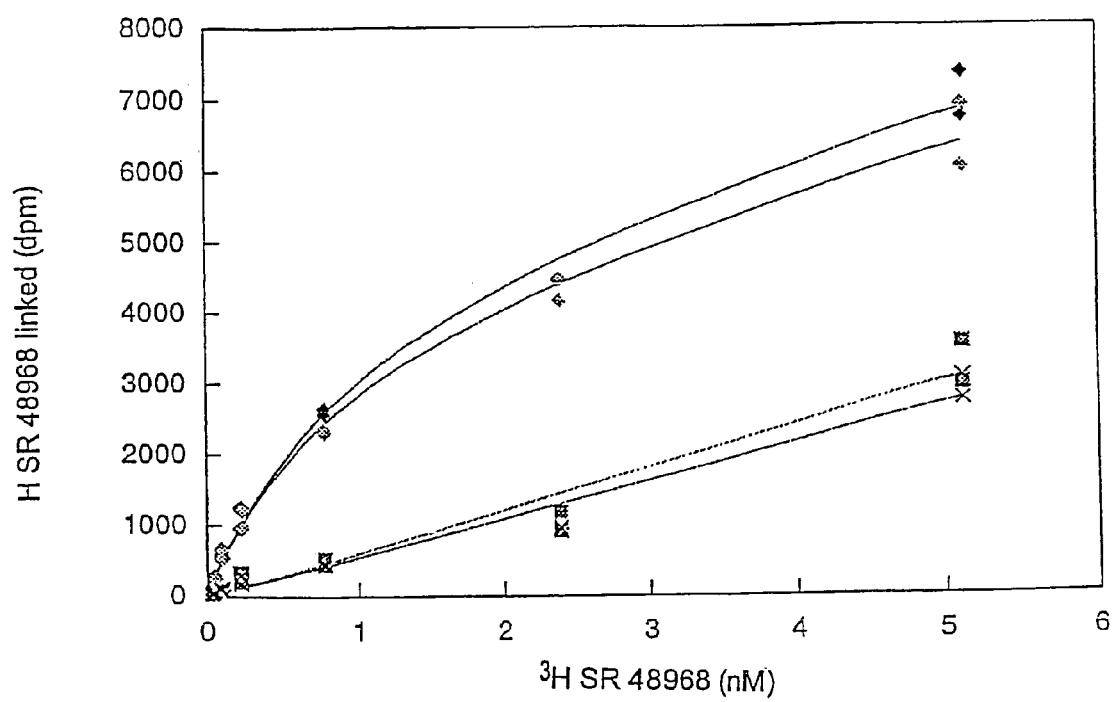

FIG. 5b represents the binding of the antagonist $^3$H SR 48968 to cells expressing the fluorescent receptor NK2R-RF1. The amount of $^3$H SR 48968 bound is given on the y-axis (in disintegrations per minute; dpm) and the concentration of $^3$H SR 48968 added to the sample is given on the x-axis. The gray and black diamonds represent the total binding of $^3$H SR 48968 in two different experiments, and the gray crosses and squares represent the non-specific binding determined in the presence of an excess of neurokinin A (10 μM). The lines correspond to the theoretical curves for the binding of a ligand to its receptor or to non-specific binding sites. The affinity values determined (KD) are 0.8 nM and 0.92 nM in each of the two experiments. The maximum binding (B max) values are, respectively, 0.075 and 0.088 pMol/25,000 cells.

Figure 6A:
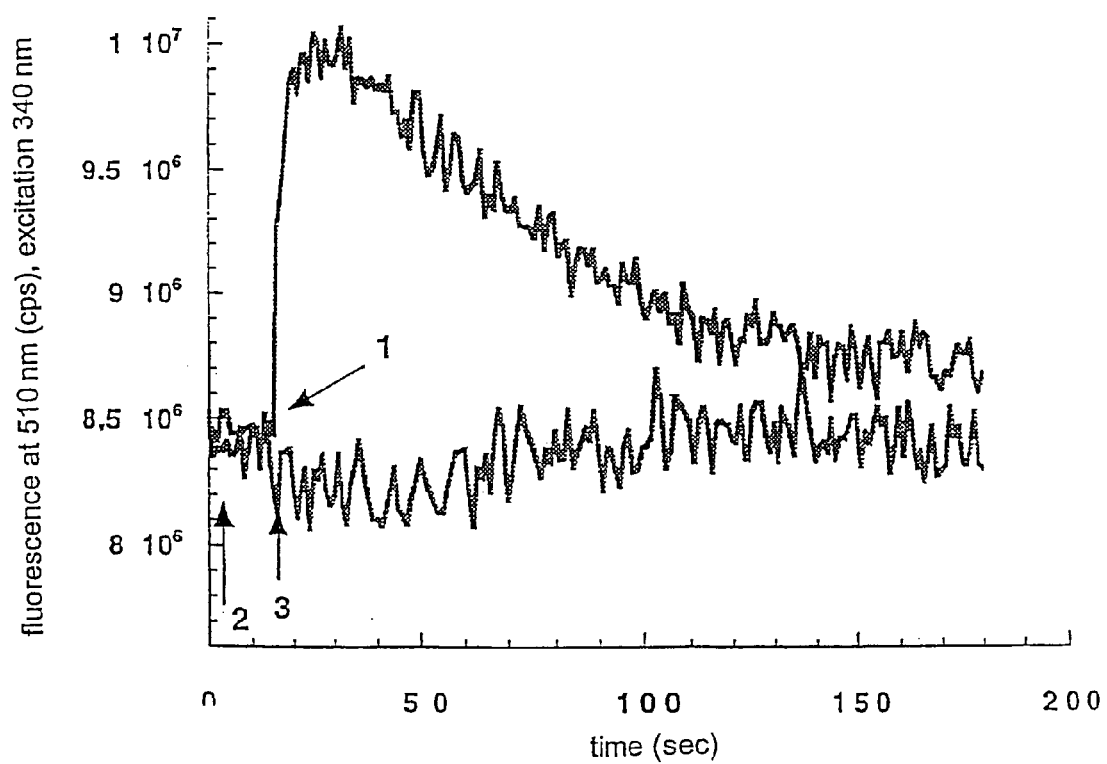

FIG. 6a represents the response functionality test for the release of intracellular calcium (FURA 2) for cells expressing the DNA construct pCEP4-NK2R WT. The fluorescence at 510 nm is given on the y-axis (expressed in counts per second), the excitation taking place at 340 nm, and the time (in seconds) is given on the x-axis. The responses are elicited by the agonist neurokinin A (NKA) and inhibited by the antagonist cyclo(-Gln-Trp-Phe-Gl-Leu-Met) (cyclopeptide). In experiment 1, 10 nM NKA are added. In experiment (2, 3), 5 μM of cyclopeptide (2), and then 10 nM of NKA (3) are successively added.

Figure 6B:
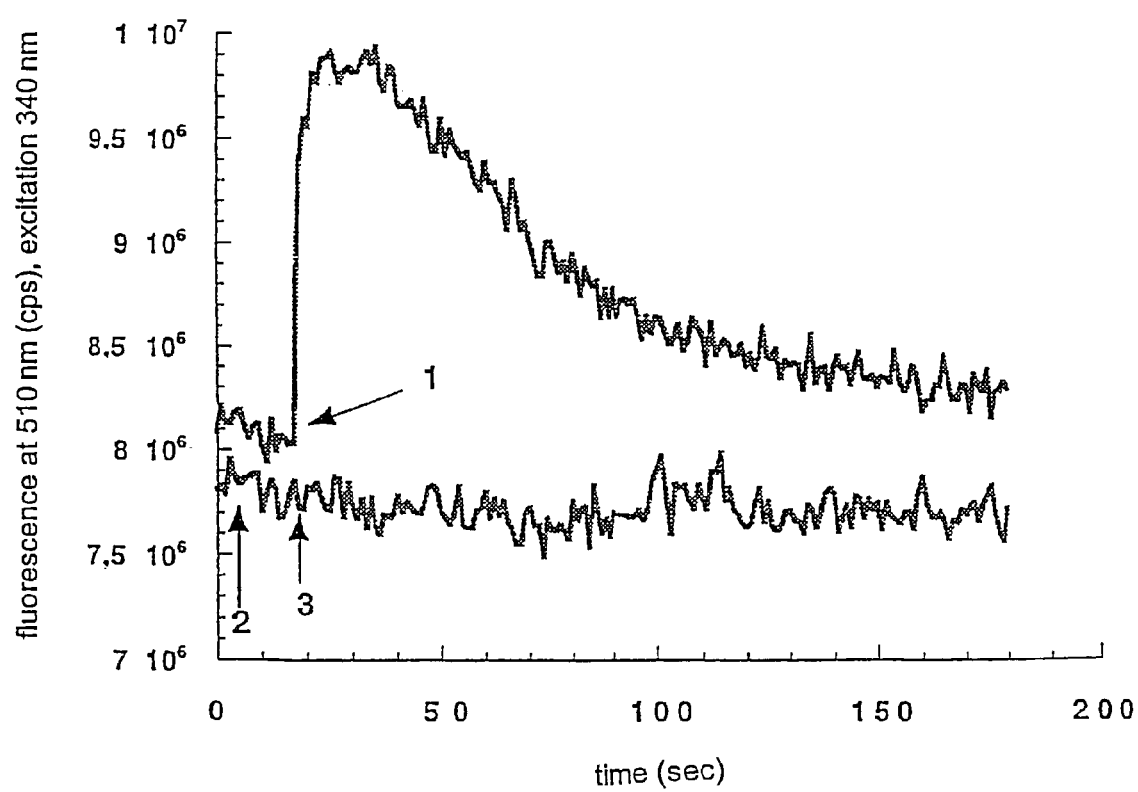

FIG. 6b represents the response functionality test for the release of intracellular calcium (FURA 2) for cells expressing the DNA construct pCEP4-NK2R—RF1. The fluorescence at 510 nm is given on the y-axis (expressed in counts per second), the excitation taking place at 340 mm, and the time (in seconds) is given on the x-axis. The responses are elicited by the agonist neurokinin A (NKA) and inhibited by the antagonist cyclo(-Gln-Trp-Phe-Gly-Leu-Met) (cyclopeptide). In experiment 1, 10 nM NKA are added. In experiment (2, 3), 5 μM of cyclopeptide (2), and then 10 nM of NKA (3) are successively added.

Figure 7:
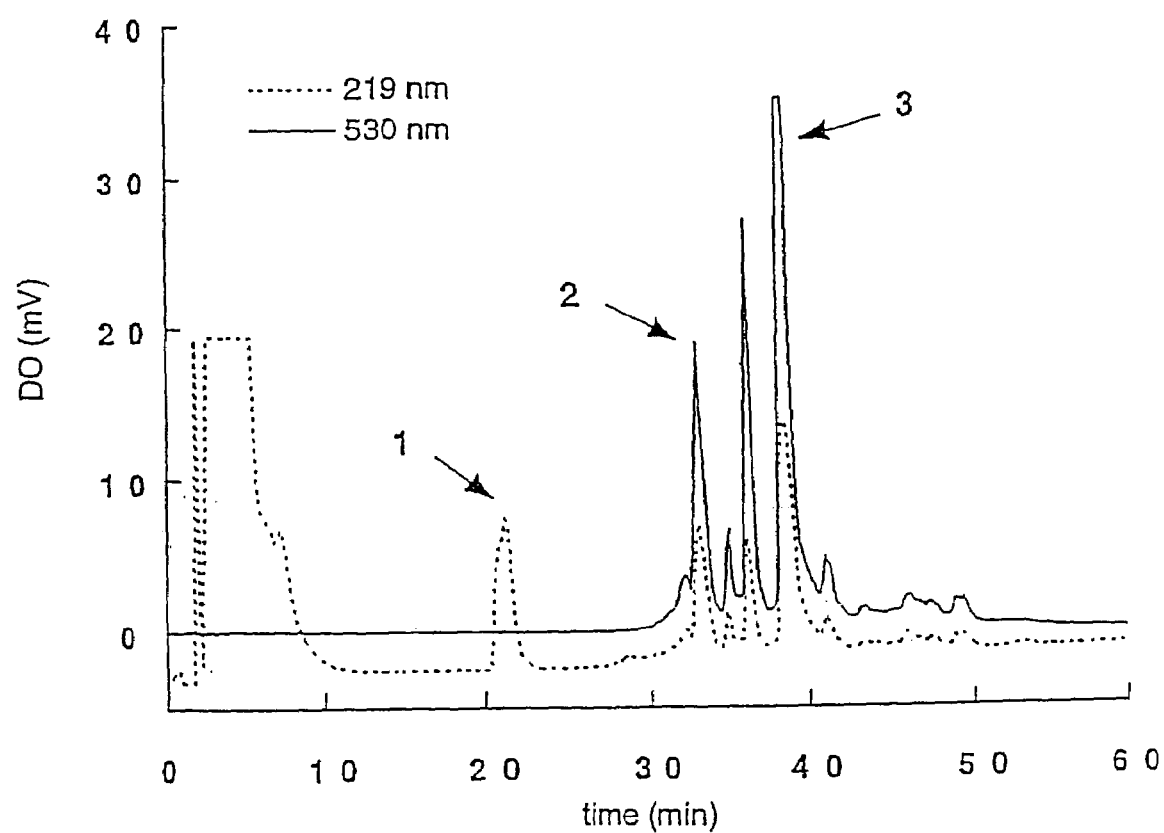

FIG. 7 represents the purification of the peptide NKA BO I by reverse-phase HPLC. The time (in minutes) is given on the x-axis and the optical density (mV) is given on the y-axis. The detection is carried out at two wavelengths: 219 nm (broken lines) and 530 nm (solid lines).

The identical peaks 1, 2 and 3 are, respectively, NKA, the NKA-Bodipy derivative and the Bodipy-IA reagent.

Figure 8A:
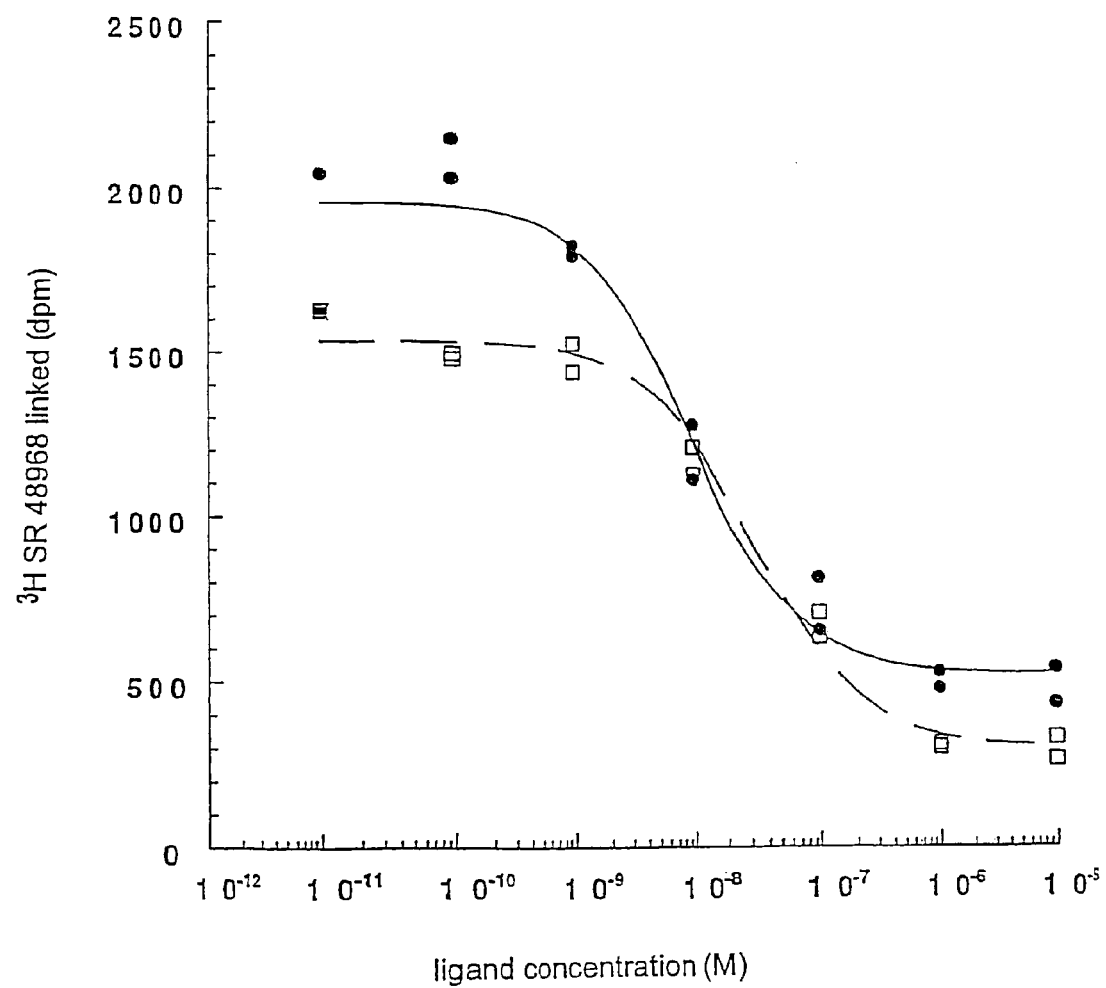

FIG. 8a represents the displacement of the binding of $^3$H SR 48968 to the receptor NK2R-WT by NKA and NKA BO I. The radioactivity (expressed in disintegrations per minute; dpm) is given on the y-axis and the concentration of ligand (M) is given on the x-axis.

The black circles represent the experiment for the displacement of $^3$H SR 48968 by NKA-BO I (KI=16.15 nM).

The white squares represent the experiment for the displacement of $^3$H SR 48968 by NKA (KI=3.03 nM).

Figure 8B:
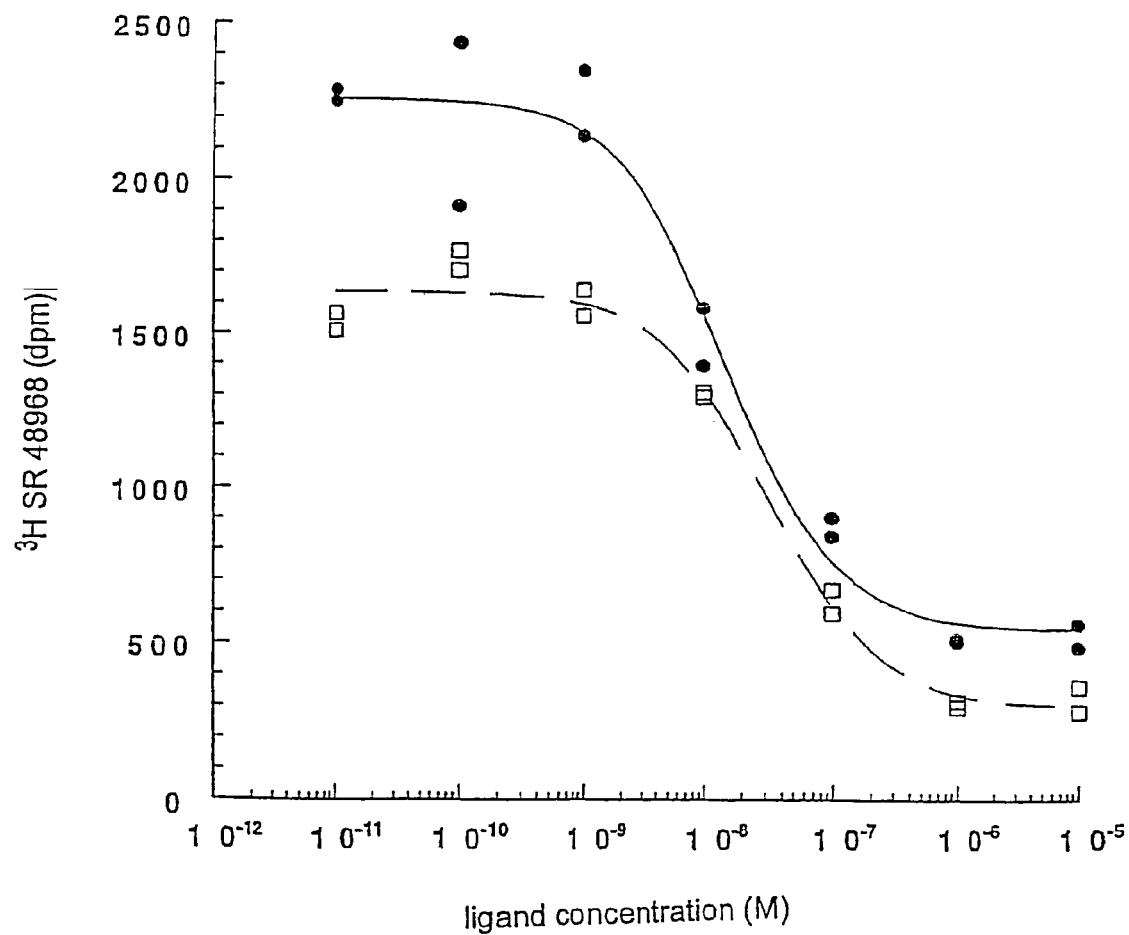

FIG. 8b represents the displacement of the binding of $^3$H SR 48968 to the receptor NK2R-RF1 by NTKA (black circles: (KI=2.1 nM) and NKA-BO I (white squares: (KI=16.08 nM). The radioactivity (expressed in disintegrations per minute; dpm) is given on the y-axis and the concentration of ligand is given on the x-axis.

Figure 9:
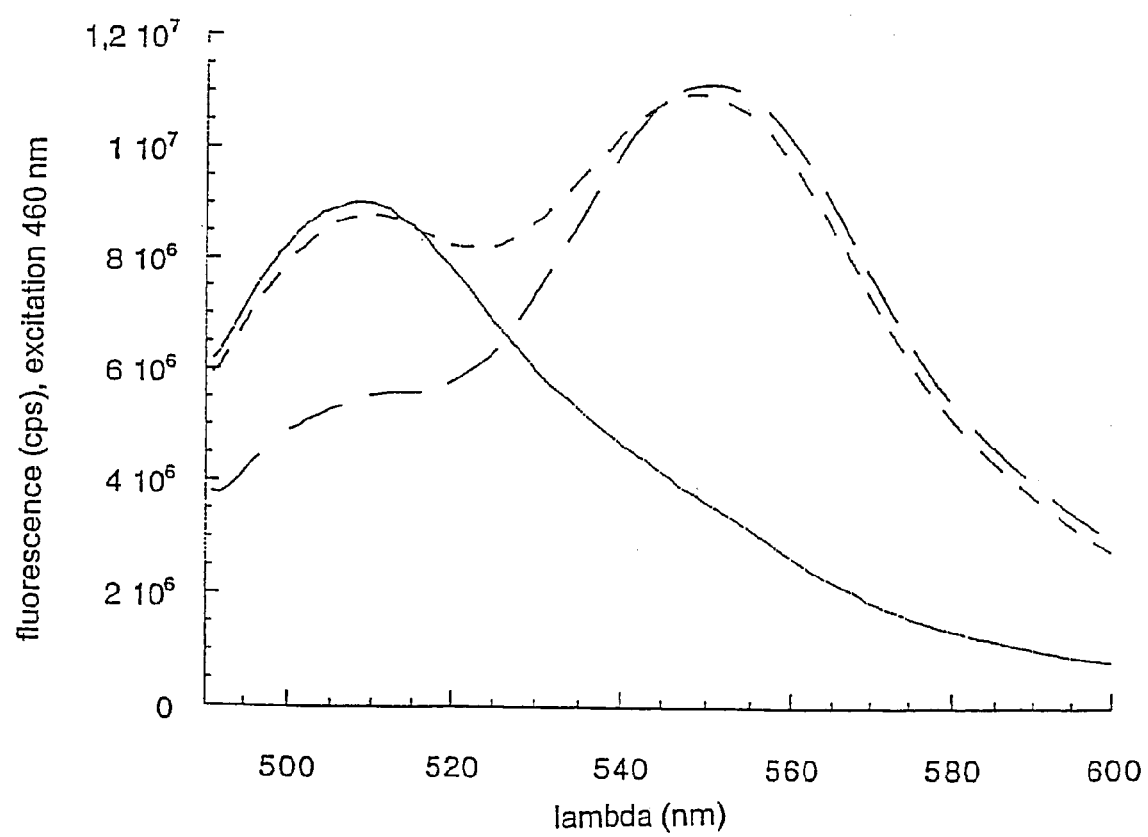

FIG. 9 represents the experiment for the energy transfer between the fluorescent ligand NKA-BO I and the fluorescent receptor NK2R-RF1 determined at equilibrium.

The solid-line curve represents the fluorescence emission (between 490 and 600 nm) of cells expressing the fluorescent receptor NK2R-RF1 (excitation at 460 nm) (Step 1).

The curve with long broken lines represents the same fluorescence emission spectrum after addition of 100 nM NKA BO I (Step 2).

The curve with broken lines represents the fluorescence emission spectrum after addition, in Step 2, of 10 µM non-fluorescent NKA. The same results are obtained after addition of 10 µM cyclo(-Gln-Trp-Phe-Gly-Leu-Met) or SR 48968.

The addition, in Step 2, of non-fluorescent NKA instead of NKA BO I has no effect on the fluorescence emission spectrum. This superimposes on the solid-line spectrum.

The fluorescence in cps is given on the y-axis and the wavelength in nm is given on the x-axis.

Figure 10:
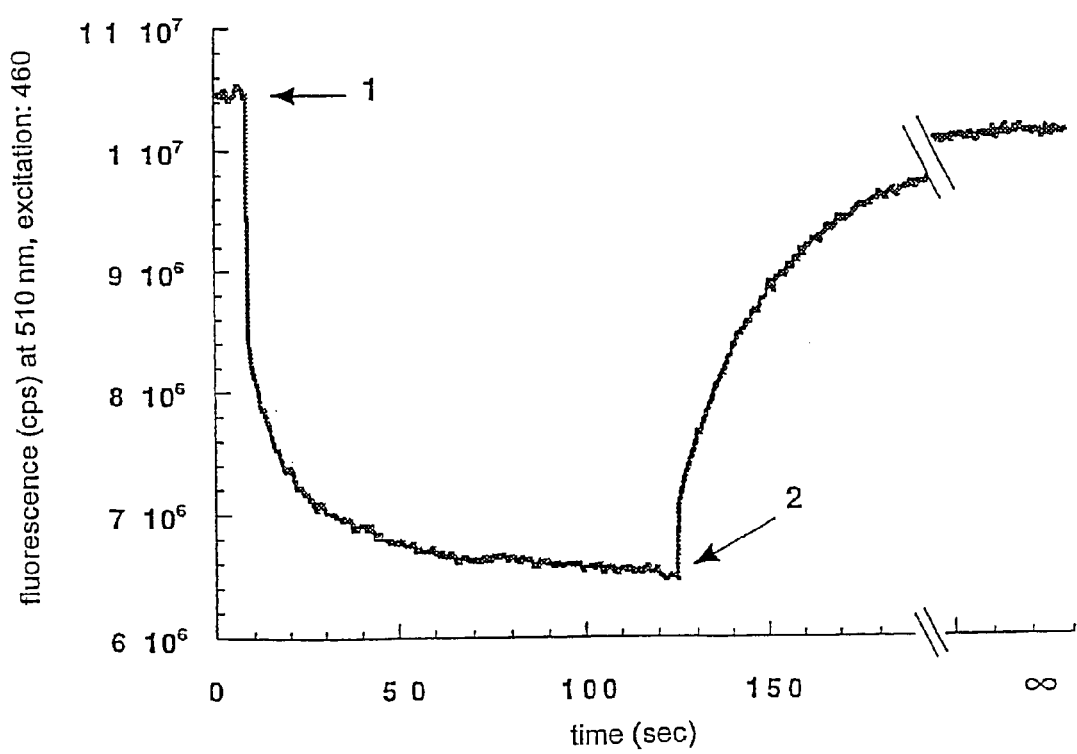

FIG. 10 represents the real-time measurement of the energy transfer between 100 nM NKA BO I and the receptor NK2R-RF1 (1), and inhibition (2) with an excess of non-fluorescent ligand (20 µM NKA or MEN 10.376 or cyclopeptide). The time in seconds is given on the x-axis and the fluorescence (in counts per second) at 510 nm is given on the y-axis, the excitation taking place at 460 nm.

The measurements are carried out using a suspension of $10^6$ cells/ml.

Figure 11A:
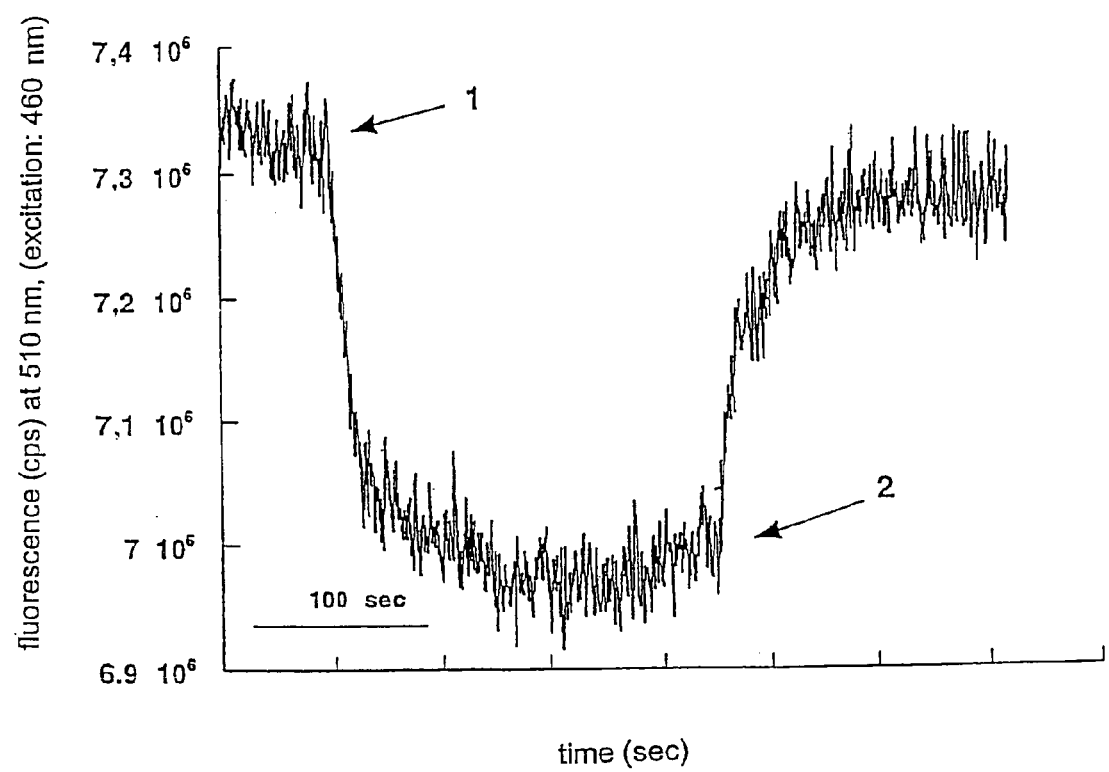

FIG. 11a represents the real-time measurement of the energy transfer between 100 nM NKA-TR and the receptor NK2R-RF1 (1), and inhibition with an excess (2) of non-fluorescent ligand (100 µM NKA or MEN 10.376 or cyclopeptide). The time in seconds is given on the x-axis and the fluorescence (in counts per second) at 510 nm is given on the y-axis, the excitation taking place at 460 nm.

Figure 11B:
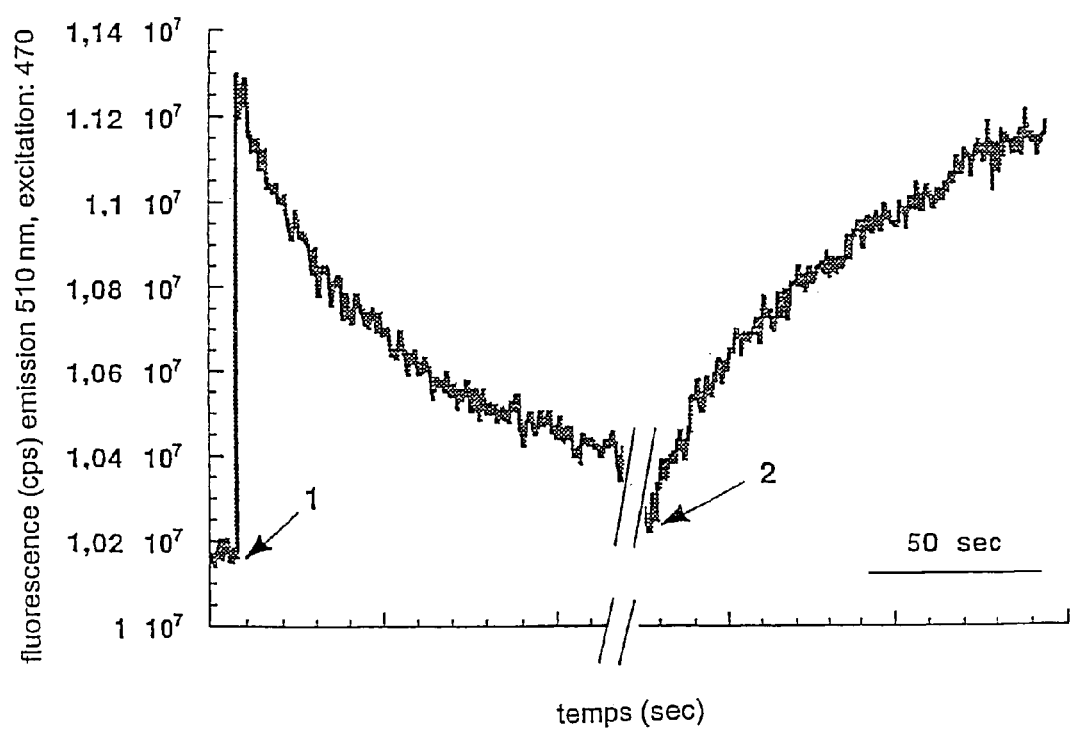

FIG. 11b represents the real-time measurement of the energy transfer between 100 nM NKA-Eos and the receptor NK2R-RF1 (1), and inhibition with an excess (2) of non-fluorescent ligand (20 µM NKA or MEN 10.376 or cyclopeptide). The time in seconds is given on the x-axis and the fluorescence (in counts per second) at 510 nm is given on the y-axis, the excitation taking place at 470 nm.

Figure 12:
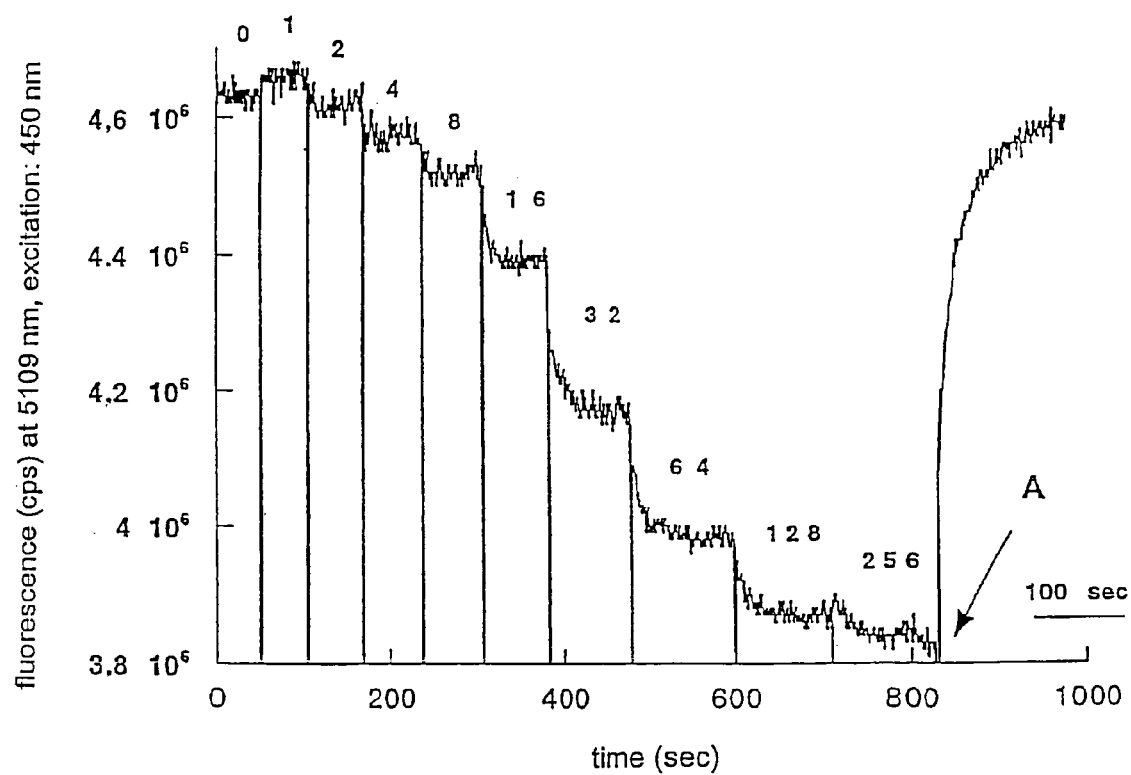

FIG. 12 represents the amplitude of the fluorescence signal as a function of the concentration of NKA BO I added (0 to 256 nM) to a suspension of cells ($10^6$ cells/ml) expressing the receptor NK2R-RF1 and inhibition with an excess (A) of non-fluorescent ligand (10 µM NKA or MEN 10.376 or cyclopeptide). The time in seconds is given on the x-axis and the fluorescence (in counts per second) at 510 nm is given on the y-axis, the excitation taking place at 450 nm.

Figure 13:
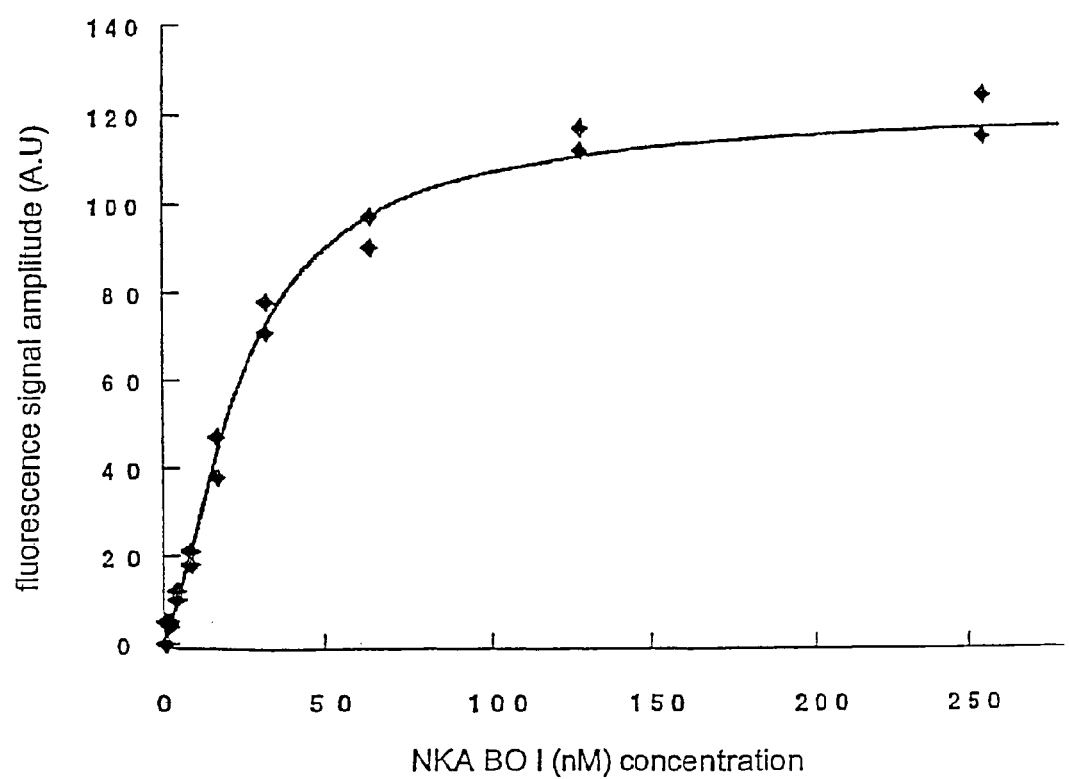

FIG. 13 represents the processing of the data from FIG. 12. The concentration of NKA BO I (nM) is given on the x-axis and the amplitude of the fluorescence signal, expressed in arbitrary units (A.U.), is given on the y-axis. The solid line represents the theoretical curve for the binding of NKA-BO I to its sites and gives an affinity value KD=24 nM.

EXAMPLES

Example 1

Figure 2:
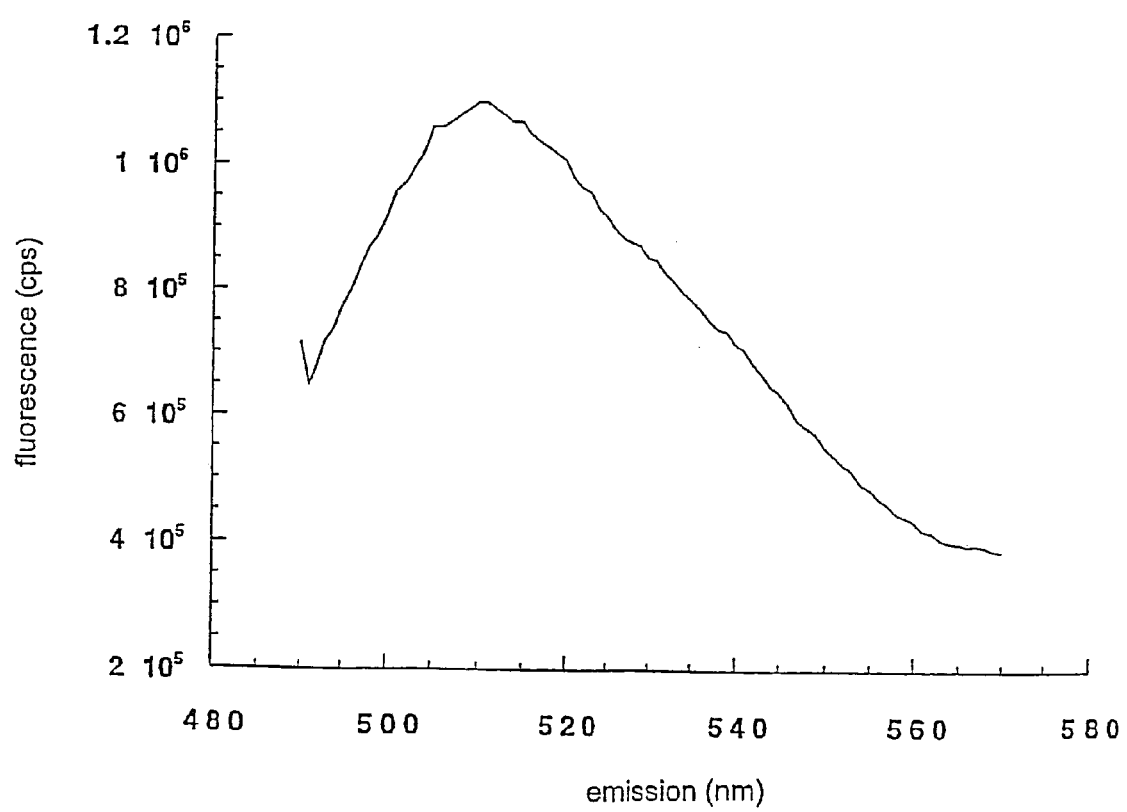
FIG. 2 represents the fluorescence measured during the expression of the construct pMT3-EGFP-C3-SP. The fluorescence expressed in counts per second (cps) is given on the y-axis and the emission wavelength is given on the x-axis. The plot shown is an emission spectrum of the difference between the measurement of the culture medium expressing EGFP and the culture medium not expressing EGFP.

DNA Constructs Comprising a Fusion Between EGFP and the Amino-Terminal End of the NK2R Receptor of Tachykinins I) Fusion of EGFP with a Signal Peptide:

The cDNA coding for EGFP (FIG. 1) is fused in phase with the sequence coding for the signal peptide of the hen alpha 7 sub-unit (Genbank Accession No: X522995) coding for an acetylcholine nicotinic receptor as follows:

A restriction site for the endonuclease BsrG I is introduced onto the coding codons 1 to 9 of EGFP using the oligonucleotide 5'GGTCGCCACCCTGTACAA-GAAGGGCGAGG3', reagents provided in the mutagenesis kit RPN 1526 (Sculptor) supplied by the Amersham company, and single-stranded pEGFP C3 prepared from the plasmid pEGFP C3 (Genbank Accession No U.S. 57607) supplied by the ClonTech company. The mutant pEGFP C3-1 obtained is sequenced and then cloned in phase with the signal peptide of alpha 7 by ligation of two fragments: the 5225-nt fragment BsrGI-Xho of pJL223 (Eiselé et al. 1993, Nature 366:479–483) and the 725-nt fragment BsrG I-Xho I of pEGFP C3-1. The plasmid pJL223 contains the gene for the protein a7-V201-5HT3 between the sites Not I and Xho I of the vector pMT3 (Swick, A. G. et al. 1992, Proc. Natl. Acad. Sci. 89:1812–1816). The construct obtained, named pMT3-EGFP-C3-SP, is transiently late expressed in HEK 293 cells (ATCC CRL 1573) after transfection with calcium phosphate (Cheng and Okayama 1986), in order to check that the construct is correct. The fluorescent emission spectrum (excitation at 450 nM) of the culture supernatants of cells expressing pMT3-EGFP C3-SP or of and transfected cells (concentrated five-fold by centrifugation on centrikon 10 Amicon)) are recorded. In FIG. 2, which shows the difference between the spectrum of transfected and non-transfected cells, the emission peak of EGFP is clearly seen, which indicates that the construct does indeed lead to the expression of EGFP secreted into the culture medium.

II) Cloning of the Receptor NK2R of Tachykinins into the Mutagenesis Vector KS and the Expression Vector pCEP4:

The 2997-nt fragment Spe I-Hind III from the plasmid prTKR1-1 (Pr. S. Nakanishi, Kyoto university, Japan, Biochem. Biophys. Res. Comm. 1989, 165:695–702), containing the cDNA coding for the rat NK2R receptor (Genbank Accession No: M31838), is ligated with the 3549-nt fragment Spe I-Hind III from the vector pBluescript KS (+) to give the plasmid pKS NK2R.

The 1369-nt fragment Not I-BsrG I from the plasmid prTKR1-1 is ligated with the 1663-nt fragment BsrG I-Xho I from pKS NK2R and the 10370-nt fragment Not I-Xho I from pCEP4 to give the plasmid pCEP4-NK2R.

Figure 3:
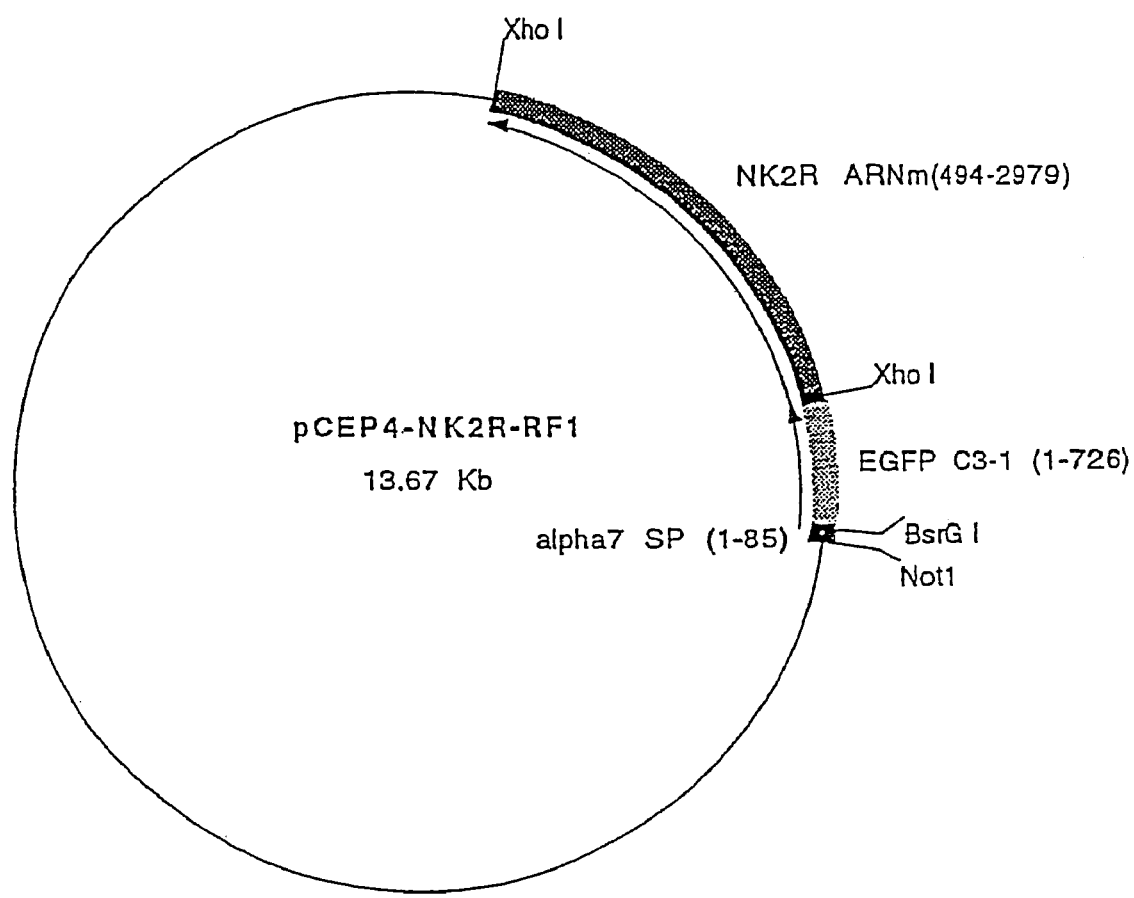
FIG. 3 represents the DNA construct pCEP4-NK2R-RF1 (13.67 kb) and comprises the sequence coding for the signal peptide of the alpha7 nicotinic receptor (alpha7 SP), EGFP (EGFP C3-1) and the NK2R receptor (NK2R ARNm) of tachykinins.

III) Fusion of EGFP Between the Signal Peptide of alpha7 and the Amino-Terminal End of the Tachykinin NK2R Receptor:

The 816-nt fragment Not I-Xho I from pMT3-EGFP C3-SP is ligated with the 12856-nt fragment Not I Xho I (Xho I partial digestion) from pCEP4-NK2R to give the construct pCEP4-NK2R-RF1 (FIG. 3).

Example 2

Construction of DNA Comprising the Fusion of GFP into the Intracellular Loops 11 and 13 of the Tachykinin NK2R Receptor I) Introduction of the EGFP Cloning Sites into the Loop i1 or i3 of the NK2R Receptor:

The single-stranded DNA of pKS NK2R is mutagenized as in la) with the oligonucleotides i1: 5'CACGAGAGGATGTACAACCTCGAGCGCA-CAGTCACC3' containing the mutations for the cloning sites BsrG I and Xho I, allowing the introduction of EGFP between amino acids 65 and 66, and i3: 5'GTACCCAGACACCAGCTAGCAGATCT-GAAGCTTCGCCATCAGGC3' containing the mutations for the cloning sites Nle I, Bgl II and Hind III allowing the introduction of EGFP between residues 233 and 234 or 233 and 238.

The plasmids obtained pKS NK2R-i1 and -i3 are introduced into competent XL1Blue bacteria (transformation), and the plasmid DNA samples isolated from the ampicillin-resistant colonies are screened for the presence of the sites introduced, respectively, by the mutations with the oligonucleotides i1 and i3.

II) Cloning of EGFP in the Loops i1 and i3 of the Tachykinin NK2R Receptor:

cloning into the loop i1: the fragments Hind III-BsrG I, and Hind III-Xho I, of pKS NK2R-i1 are ligated with the fragment BsrG I-Xho I, 725 nt, of pEGFP C3-1. The insert of 3741 nt coding for the fusion protein is then excized with the enzymes Spe I and Sal I and ligated with the vector pCEP4 opened by the enzymes Nhe I and Xho I to give the DNA construct pCEP4 NK2R-RF2;

cloning into the loop i3: two constructs are obtained:

the 744-nt fragments Nhe I-Bgl II of pEGFP C3 are ligated with the fragments Not I-Nhe I and Bgl II-Not I of pKS-NK2R-i3, the 3750-nt insert Spe I-Sal I obtained is then cloned into the vector pCEP4 between the sites Nhe I and Xho I to give the DNA construct pCEP4-NK2R-RF3.

the 757-nt fragments Nhe I-Hind III of pEGFP C3 are ligated with the fragments Not I-Nhe I and Hind III-Not I of pKS-NK2R-i3, the 3770-nt insert Spe I-Sal I thus obtained is then cloned into the vector pCEP4 between the sites Nhe I and Xho I to give the DNA construct pCEP4-NK2R-RF4.

Example 3

Expression of Recombinant Proteins and Functional Characterization

I) Expression:

HEK 293 cells are transfected, by the preparation method with calcium phosphate (Chen & Okayama 1987, Mol. Cell. Biol. 7:2745–2752, Current Protocols in Molecular Biology, op.cit.), with the DNA constructs pCEP4-NK2R-RF1, -RF2, -RF3 and -RF4 stable lines are established by selecting transfected cells resistant to hygromycin (100 µg/ml, Clontech). The cells are cultured in the presence of 100 µg/ml hygromycin in MEM medium (Gibco) supplemented with 10% fetal calf serum (Seromed), penicillin (100 units/ml), streptomycin (100 µg/ml) and glutamine (4 mM) (Methods in enzymology, Vol LVIII, 1979).

II) Measurements of the Expression and Binding Properties of the Recombinant Receptors:

a) By Fluorimetry:

The fluorescence experiments are carried out in a 1 ml tank fitted with a magnetic stirring system and placed in a Fluorolog spectrofluorimeter (SPEX) equipped with a 450 W xenon lamp (Osram) and Spex 1680 0.22 m (excitation) and Spex 1681 0.22 m (emission) monochromators. The cells or the membrane fragments are suspended in physiological buffer: 10 mM Hepes, 137.5 mM NaCl, 1.25 mM $MgCl_2$, 1.25 mM $CaCl_2$, 6 mM KCl, 5.6 mM glucose, 0.4 mM $NaH_2PO_4$, 0.1% (w/v) BSA, pH 7.4.

The whole cells are harvested after treatment with Versene (PBS, 5 mM EDTA), centrifuged for 5 min at 1000 g and RE suspended at a concentration of 250,000–1,000,000 cells/ml in physiological buffer.

FIG. 4a shows the excitation and emission spectra recorded with cells transfected with the constructs pCEP4-NK2R-WT and pCEP4-NK2R-RF1. The spectra clearly show the signal for EGFP and indicate that these constructs are indeed expressed by the HEK 293 cells. FIG. 4b shows the fluorescence emission spectra of cells expressing the wild-type receptor as well as the fusions RF1 and RF2.

b) By Binding Experiment:

The appearance of neurokinin binding sites at the surface of the cells is determined by binding 0.1 nM $^{125}I$ NKA or 1 nM $^3H$ SR48968 in PBS on the whole cells in suspension (200–500.000 cells/ml, 250 µl/test). After incubation for 30 min. at room temperature, the samples are filtered through GF/C filters (Whatmann) pre-treated in 1% powdered milk in PBS (2.7 mM KCl, 1.47 mM KH2PO4, 0.137 mM NaCl, 8.06 mM $Na_2HPO_4$), rinsed twice with PBS (4 ml) and then counted in a scintillation cocktail.

The saturation curves for the binding of 3HSR 48 968 are carried out in 10 mM Hepes, 137.5 mM NaCl, 1.25 mM $MgCl_2$, 1.25 mM $CaCl_2$, 6 mM KCl, 5.6 mM glucose, 0.4 mM $NaH_2PO_4$, 0.1% (w/v) BSA, pH 7.4 at 4° C. for 1 h 30 min. in the presence or absence of NKA at 1 µM final. Each 500 µl sample contains 25,000 cells, and the fraction of bound ligand is less than 10% of the amount added to each tube. Filtration is carried out at the end of incubation, as described above. FIGS. 5a and 5b shows the binding curves (in dpm bound) obtained with increasing concentrations of the ligand $^3HSR$ 48968 on, respectively, cells expressing the wild-type receptor (NK2R WT) or the N-terminal fusion with EGFP (NK2R-RF1). The ligand exhibits the same affinity for the two receptors and the number of binding sites expressed at the surface of the cells is comparable.

III) Functional Tests:

I) Measurement of the Cytosolic Calcium using FURA 2:

The fluorescent calcium-chelating agent, FURA 2 acetyl methyl ester (Molecular Probes), dissolved in DMSO is diluted to a concentration of 3 µM in 10 mM Hepes, 137.5 mM NaCl, 1.25 mM $MgCl_2$, 1.25 mM $CaCl_2$, 6 mM KCl, 5.6 mM glucose, 0.4 mM $NaH_2PO_4$, 0.1% (w/v) BSA, pH 7.4 buffer. The cell culture medium is aspirated and then replaced with 7 to 10 ml of FURA 2 AM solution. The cells are placed in the $CO_2$ incubator for 45 min. The medium is then aspirated, replaced with FURA-free Hepes buffer and the cells are replaced in the $CO_2$ incubator for a further 15 min. The buffer is aspirated and the cells are then collected after they have been detached from the dish with a 5 mM EDTA, PBS solution for 5 min. After centrifugation at 1000×g for 5 min., the cell pellet obtained is re-suspended at a rate of $1 \times 10^6$ cells/ml in Hepes buffer.

The calcium-release measurements are carried out at 37° C., in a spectrofluorimetiy tank containing a magnetic stirrer bar. The excitation wavelength is set at 340 µm and the emission wavelength is set at 510 nm.

FIG. 6 shows the results obtained during the stimulation of cells transfected with the construct coding for the wild-type receptor (6a) and of cells transfected with the construct pCEP4-NK2R-RF1 (6b). The responses elicited with neurokinill A are inhibited by the specific NK2R agonists SR 48968 (Sanofi recherche), MEN 10,376 (Bachem) or the cyclopeptide cyclo(-Gln-Trp-Phe-Gly-Leu-Met) (Bachem). Neurokinin A does not elicit any response on non-transfected HEK 293 cells.

Preparation of Membrane Fragments:

The membrane fragments are prepared by homogenizing the cells using a tissue homogenizer (Potter or Ultra-Turrax) in the presence of a mixture of protease inhibitors, at 4° C. The cells are centrifuged at 1000×G for 5 min. and then re-suspended in membrane preparation buffer: 50 mM Tris HCl, 1 mM EDTA-Na, 10 mM DTT, containing the protease inhibitor cocktail Complete (Boeliringer). The suspension is homogenized using a Potter homogenizer at 4° C. After centrifugation at 3000×G for 10 min., the supernatant is collected and the pellet is taken Up in the above buffer, re-homogenized and re-centrifuged at 150,000×g for 30 min. The pellets obtained are re-suspended in membrane preparation buffer at a concentration of 6–10 mg prot/ml.

Example 4

Preparation of Fluorescent Ligands

I) Preparation of Fluorescent Neurokinin A:
a) Bodipy 530/560 Group:
The lyophilized NKA is dissolved in DMF at 10 mM final. 10 μmol of NEt$_3$ (200 mM in CH$_3$CN), i.e. 100 μL, are added to 50 μL of this solution (50 μMol, 50 μL), followed by 15 μL of BODIPY 530/550 IA [N-(4,4-difluoro-5,7-dimethyl-4-bora-3a,4a-diaza-s-indacene-3-propionyl)-N'-iodoacetyl-ethylenediamine] dissolved in DMF at a rate of 0.3 μMol per 10 μL. The mixture is vortexed and then left at room temperature. After 24 hours, the reaction product is purified by HPLC (Gilson) on a Z5C8 25F reverse-phase column (Zorbax) on which is developed a linear gradient of from 10 to 95% solvent B over 60 minutes (A: H$_2$O 0.1% TFA; B: CH$_3$CN 0.1% TFA) with a flow rate of 1 ml/min. The detection wavelengths are set at 219 nm (peptide) and 530 nm (fluorophore). The product eluted (NKA BO I) at time 34 min. (FIG. 7) is collected, concentrated by evaporation and re-suspended in DMF.

b) Coumarin and Eosin Groups:
The reaction conditions used for labeling neurokinin A with the coumarin derivative (7-diethylamino-3-((4'-(iodoacetyl)amino)phenyl)-4-methylcoumarin) and the eosin derivative (eosin-5-iodoacetamide) are the same as in a). The purifications are carried out on a Z5C8 25F reverse-phased column (Zorbax) on which is developed a linear gradient of from 10 to 95% solvent B over 60 minutes (A: H$_2$O 0.1% TFA; B: CH$_3$CN 0.1% TFA) with a flow rate of 1 ml/min. The coumarin derivative of NKA (NKA-Coum) is eluted at time 25 min., while the eosin derivative of NKA (NKA-Eos) is eluted at time 27 min.

c) Sulforhodamine 101 Group:
The reagent used is sulforhodamine 101 acid chloride (Aldrich, or Texas Red sold by Molecular Probes). The protocol is the same as that for the grafting of BODIPY 530/550 IA. The purification is carried out by HPLC on a Z5C8 25F reverse-phase column (Zorbax) on which is developed a linear gradient of from 10 to 95% solvent B over 60 minutes (A: H$_2$O 0.1% HFBA; B: CH$_3$CN 0.1% HFBA) with a flow rate of 1 ml/min. The detection wavelengths are set at 219 nm (peptide) and 590 nm (fluorophore). The product eluted (NKA TR) at time 40–41 min. is collected, concentrated by evaporation and re-suspended in DMF.

Example 5

Detection of the Interaction Between the Fluorescent NK2R Receptor and its Fluorescent Ligands I) By Displacement of a Radioligand (Competition Experiment):
The curves for the displacement of the binding of $^3$HSR 48968 with a non-radioactive ligand are carried out in 10 mM Hepes, 137.5 mM NaCl, 1.25 mM MgCl$_2$, 1.25 mM CaCl$_2$, 6 mM KCl, 5.6 mM glucose, 0.4 mM NaH$_2$PO$_4$, 0.1% (w/v) BSA, pH 7.4 buffer at 4° C. for 1 h 30 min. in the presence or absence of NKA at 1 μM final. Each 500 μl sample contains 25,000 cells, 1 nM 3HSR 48968 and a non-radioactive ligand at various concentrations (from 1 nM to 10 μM). The incubation is carried out for one hour at 4° C. Filtration is carried out at the end of incubation, as described in 3b).

FIG. 8 shows the curves for the displacement of the radioligand $^3$HSR 48968 with neurokinin A (NKA) and NKA BO I on, respectively, HEK 293 cells expressing the wild-type NK2R receptor (construct pCEP4-NK2R, FIG. 8A) or the fusion of EGFP at the N-terminal of the NTK2R receptor (construct pCEP4-NK2R-RF1, FIG. 8b). The points represent the bound radioactivity (in dpm) in the presence of variable concentrations of NKA or NKA BO I. The affinity values derived from these curves indicate that NKA (just like NKA BO I) binds with the same affinity to the wild-type receptor and to the receptor rendered fluorescent. The affinity values are, for NKA: KI=3 nM on the wild-type receptor and 2.1 nM on the fluorescent receptor, and for NKA BO I: KI=16 nM on the wild-type receptor and 16 nM on the fluorescent receptor. The same measurements carried out with the antagonist MEN 10.376 give the affinity values: KI=53 nM on the wild-type receptor and KI=61 nM on the fluorescent receptor.

II) By Energy Transfer:
a) Interactions Between NKA BO I and the NK2R-RF I Receptor at Equilibrium:
The HEK293 cells expressing the NK2R-RF1 are suspended at a concentration of 1,000,000 cells/ml in Hepes physiological buffer (10 mM Hepes, 137.5 mM NaCl, 1.25 mM MgCl$_2$, 1.25 mM CaCl$_2$, 6 mM KCl, 5.6 mM glucose, 0.4 mM NaH$_2$PO$_4$, 0.1% (w/v) BSA, pH 7,4). The cells are then placed in a fluorescence tank at a concentration which can range from 100,000 to 1,000,000 cells/ml. An emission spectrum of these cells is recorded between 490 and 600 nm (excitation at 460 nm) and NKA BO I is then added to a final concentration of 100 nM. The emission spectrum of the solution is again recorded. An excess (1–10 μM) of non-labeled ligand specific for NK2R receptor (non-labeled NKA) or for SR 48968 (Sanofi Recherche) or for the cyclic peptide, cyclo(-Gln-Trp-Phe-Gly-Leu-Met), is then added and the emission spectrum of the solution is again recorded. FIG. 9 shows the three spectra superimposed, on which an extinction of the fluorescence of EGFP (peak at 510 nm) during the addition of NKA BO I and a return to the initial fluorescence during the subsequent addition of non-labeled ligand are clearly detected. The appearance of a peak at 550–560 nm during the addition of the fluorescent ligand and a reduction in its intensity during the addition of non-labeled ligand are also detected. These results indicate the occurrence of a transfer of energy between the fluorescent receptor and its fluorescent ligand. The signal is reversible by means of addition of a pharmacological agent capable of inhibiting the interaction between the ligand and its receptor. The addition of non-fluorescent NKA to cells which express the fluorescent receptor NK2R-RF1 has no effect on the fluorescence emission spectrum.

b) Real-Time Interactions Between NKA BO I and NK2R-RF1:
The same recordings can be made in real time. For this, the excitation wavelength is set at 460 nm and the emission wavelength is set at 510 nm. The addition of NKA BO I to the cell suspension entails a reduction in the fluorescence intensity at 510 mm and the subsequent addition of an excess of non-labeled ligand re-establishes the fluorescence to its initial value (see FIG. 10). The final value of the fluorescence intensity can be higher than the initial value when the absorption of the fluorescent ligand contributes to the signal.

This is observed with the NKA BO for concentrations of greater than 200 nM, when the cell concentration is of the order of $5\times10^5$ to $1\times10^6$ cells/ml. Finally, the addition of non-fluorescent NKA at time 0 has no effect on the intensity of the signal measured at 510 nm.

c) Detection of the Interaction between the NK2R-RF1 Receptor and the Ligands NKA TR and NKA Eos:

Reproduction of the experiment described in a) with NKA TR (FIG. 11a) or NKA Eos (FIG. 11b) indicates that the detection of an NK2R-RF1 receptor-fluorescent ligand interaction signal is not restricted to the EGFP-BODIPY couple but can also be extended to the EGFP-sulforhodamine 101 or EGFP-Eosin couple.

d) Experiment of Saturation of the Binding of NKA BO I to its Receptor Sites:

Given that the amplitude of the signal recorded according to the description in 8b (FIG. 12) is proportional to the concentration of NKA BO I added, measurements of the amplitude of the specific signal can be carried out as a function of the concentration of ligand added. FIG. 12a shows the variation in the amplitude of the signal when the concentration of NKA BO I ranges from 0 to 256 nM, by successive addition of aliquots of a $10^{-5}$ M stock solution to a suspension of 1 ml of cells at a concentration of $10^6$ cells/ml in Hepes physiological buffer. The processing of the experimental data (FIG. 12b) makes it possible to extract an affinity value for NKA BO I (KD=20–30 nM) which is in excellent agreement with the measurements taken by displacing a radioligand, as described in Example 5, I).

e) Competition Experiment:

The membrane fragments containing the NK2R-RF1 receptor, prepared according to the process described in Example 3, in the section on the preparation of membrane fragments, are diluted in Hepes buffer (10 mM Hepes, 137.5 mM NaCl, 1.25 mM MgCl2, 1.25 mM $CaCl_2$, 6 mM KCl, 5.6 mM glucose, 0.4 mM NaH2PO4, 0.1% (w/v), BSA pH 7.4) in a proportion of 20 µL of membranes/ml. Aliquots of the membranes are incubated in the presence of NKA, MEN 10.376, cyclo(-Gln-Trp-Phe-Gly-Leu-Met) or SR 48968 at various concentrations. After incubation for 30 minutes, the samples are placed in a spectrofluorimetry tank and the signal generated by addition of 25 nM NKA BO I is recorded for 120 sec. at 510 nm, the excitation wavelength having been set at 470 nm. Since the amplitude of the signal elicited by the interaction between the NK2R-RF1 receptor and its ligand NKA BO I is proportional to the number of binding sites accessible to the fluorescent ligand, it is possible to establish a curve of the displacement of NKA BO I by the non-fluorescent ligand.

The process can also be performed by simultaneous mixing of the membrane fragments containing the NK2R-RF1 receptor, the ligand NKA BO I and the non-labeled ligand. The mixture is then incubated for the time required to reach the binding equilibrium (30–60 min.) and the fluorescence is measured at 510 nm, the excitation wavelength being set at 470 nm. The same experiments can be carried out with whole cells at a concentration of 250,000 to 1,000,000 cells/ml.

Example 6

Cloning of the NK2R-RF1 cDNA into the Vector PPIC9 and Expression in the Yeast *Pichia Pastoris* a) Cloning:

The portion of pCEP4-NK2R-RF1 coding for the fusion protein is amplified by PCR (Current Protocols in Molecular Biology, op.cit.) using the primers 5'GGAGAGTTCCAACTCGAGAAAAGAAA-GAAGGGCGAGGAG3' and

5'GTCAGCTGTTTCTGCGGCGCGCTAAGC-CTGGGCCTT3' allowing 1) the production of 1868-nt fragment coding for all of the fusion protein NF2R-EGFP except for the signal peptide, and 2) the in-phase cloning into the expression vector of yeast pPIC9 (Invitrogen) with the sequence coding for the signal peptide of the promoter factor alpha of the gene AOX1. The cloning sites used are, respectively, XhoI for the 5' end of the amplification product and Not I for its 3' end.

b) Expression:

The yeasts are transformed with the linearized pPIC9-NK2R-RF1 plasmid (StuI or SalI) and are cultured on histidine-free MD culture medium, prepared according to the instructions in the manual supplied with the vector pPIC9 (in Vitrogen). The expression of the DNA construct introduced into the cells is induced with methanol. For this, the colonies are propagated in liquid medium (BMGY) for 24 h, and are then transferred into BMMY medium containing 0.5% methanol, allowing induction of the expression of the DNA construct NK2R-RF1. Aliquots of these cultures are withdrawn and the clones expressing the fluorescent protein identified by measuring the excitation and emission spectra of EGFP.

Example 7

Construction of DNA Coding for the Muscarinic Receptor of Acetylcholine Fused with EGFP and Expression in Mammalian Cells I) Cloning: the cDNA fragment coding for the human muscarinic receptor M1 (Genbank Accession No X15263) is amplified by PCR (Current Protocols in Molecular Biology, op.cit.) using the primers:

5'TTAGTTCTAAACTAGCGGCCGCAC-TAGTCCTCCATGAACACTTCAGC CCCA3' and

5'CTTGAACCTATAGCTAGCCTCGAGTCAG-CATTGGCGGGAGGG3'.

The 1383-nt fragment obtained is cleaved with the enzymes Not I (at the 5' end) and Xho I (at the 3' end) and ligated with the KS vector opened with the same enzymes (2888-nt fragment) to give the construct KS-hM1, or ligated with the vector pCEP4 opened with the same enzymes to give the construct pCEP4-hM1.

The construct KS-hM1 is used for the production of single-stranded DNA (Current Protocols in Molecular Biology, op.cit.) and the production of mutants.

II) Fusion of EGFP at the N-Terminal of the hM1 Receptor.

The oligonucleotide 5'CCTGCTGTCTCAGATCTCAT-CACCGTCC3' is used, together with the reagents in the Sculptor mutagenesis kit (Amersham), to produce a mutant which allows the fusion in position 13 of the sequence coding for the hM1 receptor by means of the introduction of a restriction site for the enzyme Bgl II.

The mutant obtained is digested with the enzymes Bgl II and Xho I and the 1354-nt generated is ligated with the 812-nt Not I-Bgl II fragment of pCEP4-NK2R-RF1, and the vector pCEP4 opened with the enzymes Not I and Xho I, to give the DNA construct pCEP4-hM1-RF1.

III) Expression of the Fusion Protein and hM1-RF1.

The plasmid pCEP4-hM1-RF1 is introduced into HEK 293 cells by transfection with calcium phosphate or into Cos 1 cells by electroporation (Current Protocols in Molecular Biology, op.cit.).

The expression of the protein is detected as described above.

IV) Synthesis and Purification of the Muscarinic Ligand ABT-Bodipy.

The base ABT (3-[2'-aminobenzhydryloxy]tropane) is dissolved in DMF (10 mM). 20 µl of this solution (0.2 µMol) are mixed with 4 µl of a 100 mM solution of Bodipy-IA and left at room temperature for 20 h. The reaction product is purified by HPLC (Gilson) on a Z5C8 25F reverse-phase column (Zorbax) on which is developed a linear gradient of from 10 to 95% solvent B over 60 minutes (A: $H_2O$ 0.1% TFA; B: $CH_3CN$ 0.1% TFA) with a flow rate of 1 ml/min. The detection wavelengths are set at 219 nm (peptide) and 530 nm (fluorophore). The product eluted (ABT Bo) at time 34 min. (FIG. 7) is collected, concentrated by evaporation and re-suspended in DMF.

Example 8

DNA Construct Coding for Fluorescent Nicotinic Receptors a) DNA Construct Coding for the Fusion of EGFP in the MIR Region of the a7-V201-5HT$_3$ Receptor.

The plasmid pJL223 (Eiselé et al. 1993, Nature 366: 479–483) contains the gene for the protein a7-V201-5HT3 which forms a receptor channel that is activated by acetylcholine and nicotine during its expression in *Xenopus ovocytes*. The coding cDNA is between the sites Not I and Xho I of the vector pMT3 (Swick, A. G. et al. 1992, Proc. Natl. Acad. Sci. 89:1812–1816).

The 1424-nt insert Not I-Xho I is cloned between the sites Not I and Xho I of the Bluescript vector and the plasmid obtained (KS 223) serves as a matrix for the production of single-stranded DNA.

The oligonucleotide

5'CAGATCATTAGTTGTACAGGAAAGATCTTGAGGATCCTGGAGTGAAG3' is used to introduce, on KS223, the restriction sites for the enzymes Bsrg I, Bgl II and BamH I in the same phase as that of the identical sites borne by the plasmid pEGFP-C3. The mutation is introduced into a region of the receptor known as the MIR (Major Immunogenic Region, Barkas et al. 1987, Science, 235:77–80) between amino acids 63 and 64.

The fragments Not I-BsrG I (267 nt) and Bgl II-Xho I (1147 nt) of this mutant of KS 223 are ligated with the fragment BsrG I-Bgl 11 (721 nt) of pEGFP—C3 and the vector pCEP4 opened by the enzymes Not I and Xho I, to give the DNA construct pCEP4-223-RF1.

The fragments Not I-BsrG I (267 nt) and BamH I-Xho I (1138 nt) of this mutant of KS 223 are ligated with the fragment BsrG I-BamH I (772 nt) of pEGFP—C3 and the vector pCEP4 opened by the enzymes Not I and Xho I, to give the DNA construct pCEP4-223-RF2.

b) Construction of DNA Coding for the Fusion of EGFP in the Cytoplasmic Region of the Receptor α7-V201-5HT$_3$ The cDNA coding for the protein α7-V201-5HT$_3$ contains in its cytoplasmic domain the sequences of the sites Avr II and Pst I, respectively, in phase and cohesive with the sequences cleaved by the enzymes Nhe I and Pst I of the plasmid pEGFP-C2 (ClonTech) and allow the production of the fusion protein containing the sequence of EGFP in the cytoplasmic domain of the protein α7-V201-5HT$_3$.

The DNA construct coding for this fusion protein is thus obtained by ligating the fragments Not I-Avr II (1036 nt) and Pst I-Xho 1 (286 nt) of KS 223 with the fragment Nhe I-Pst 1 (774 nt) of pEGFP—C2 and the vector pCEP4 opened by the enzymes Not I and Xho I to give the construct pCEP4-223-RF3.

The constructs pCEP4-223-RF1, -RF2, and -RF3 are then expressed in HEK 293 cells as defined above.

What is claimed is:

1. A process for detecting and/or quantifying non-covalent interactions between a target receptor and one of its ligands, comprising:

preparing cells or cell fragments containing a nucleic acid sequence encoding a fluorescent protein fused with a nucleic acid sequence encoding the target receptor, the fusion between the nucleic acid sequence for the fluorescent protein and the nucleic acid sequence for the target receptor being such that the properties of the target receptor are not modified by the presence of the fluorescent protein:

wherein the interaction between the target receptor, and the ligand is not modified, and wherein a response transduction function is not modified, the fluorescent protein is selected from Green Fluorescent Proteins (GFPs) obtained or derived from autofluorescent proteins of Cnidarians, the molar extinction coefficient of which is greater than about 14,000 $M^{-1}$ $cm^{-1}$ and the quantum fluorescence yield is greater than about 0.38 placing said cells or said cell fragments in contact with a ligand for said target receptor, said ligand labeled with a label capable of absorbing the light emitted by the fluorescent protein, the fluorescent protein being the fluorescence energy donor and the label being the fluorescence energy acceptor, or the fluorescent protein being the fluorescence energy acceptor and the label being a fluorescent substance which is a fluorescence energy donor; and irradiating said cells or said cell fragments at a wavelength which makes it possible either to excite the fluorescent protein or to excite the label, wherein the steps of placing in contact and irradiating are carried out either simultaneously or one after the other, or said cells or said cell fragments are placed in contact with a ligand for said target receptor said ligand labeled with a label, the cells or the ligand having been irradiated before being placed in contact, wherein a reduction in the amplitude of the donor's emission and/or emission signal characteristic of the acceptor's emission is measured and measuring the fluorescence energy transfer when quantifying the non-covalent interactions.

2. The process according to claim 1, wherein the target receptor is selected from the group consisting of:

membrane-bound G protein coupled receptors (GPCRs),
insuline-like growth factor (IGF) receptors,
ion channel-receptors, and
intracellular nuclear receptors.

3. The process according to claim 1, wherein the fluorescent protein is enhanced green fluorescent protein (EGFP) and the is Bodipy and in which either the reduction in the emissions amplitude of EGFP or an emission signal of Bodipy resulting from an energy transfer is detected, the irradiation wavelength corresponding to the excitation wavelength of EGFP.

4. The process according to claim 1, wherein the fluorescent protein is enhanced green fluorescent protein (EGFP) and the label is coumarin, and wherein either the diminution of amplitude of coumarin or an emission signal EGFP resulting from an energy transfer is detected, said irradiation wavelength corresponding to the excitation wavelength of coumarin.

5. The process according to claim 1, wherein the fluorescent protein is fused on its N-terminal side to the C-terminal side of the target receptor.

6. The process according to claim 1, wherein the fluorescent protein is fused on its C-terminal side to the N-terminal side of the target receptor.

7. The process according to claim 1, wherein the fluorescent protein is inserted into a target G protein coupled receptor (GPCR), this insertion taking place in the first or third intracellular loop of the receptor, with the proviso that the insertion does not destroy either the properties of the receptor or the fluorescence of the fluorescent protein.

8. The process according to claim 1, wherein the cells are mammalian cells, which are adherent or in suspension selected from the group consisting of HEK 293 cells, CHO cells, COS cells, lyphocytic lines, fibroblasts, yeast cells selected from *Pichia pastoris, Saccharomyces cerevisia, Saccharomyces kluyveri, Hansenula polymorpha*, and insect cells.

9. The process according to claim 1, wherein a signal can be detected after mixing the compound being a fluorescence energy donor and the compound being a fluorescence energy acceptor, and can be abolished by the addition of a non-fluorescent substance having the same binding site, and wherein a signal/noise ratio is greater than about 2.

10. The process according to claim 1, wherein the label for the ligand is selected from:
Green Fluorescent Proteins (GFPs) obtained or derived from autofluorescent proteins of Cnidarians, the molar extinction coefficient of which is greater than about 14,000 $M^-$ $cm^{-1}$ and the quantum fluorescence yield is greater than about 0.38,
fluorescent chemical compounds, and
non-fluorescent chemical compounds belonging to the Acid Violet group, Acid Red group, alizarins, aluminon, azocarmines, basic fuchsin, Bordeaux R and Carmine.

11. The process according to claim 1, wherein the fluorescent protein is selected from: green fluorescent protein (GFP) or enhanced green fluorescent protein (EGFP), cyan fluorescent protein (CFP) or enhanced cyan fluorescent protein (ECFP), yellow fluorescent protein (YFP) or enhanced yellow fluorescent protein (EYFP), and green fluorescent protein UV (GFPUV).

12. A process for detecting and/or quantifying non-covalent interactions between a target receptor and one of its ligands, comprising:
providing a fluorescent protein fused with a target receptor of a cell, wherein,
the fusion does not affect either the interaction between said target receptor and a ligand for said receptor or a response transduction function, and
said fluorescent protein is a Green Fluorescent Protein obtained or derived, from autofluorescent proteins of Cnidarians having a molar extinction coefficient greater than about 14,000 $M^{-1}$ $cm^{-1}$ and a quantum fluorescence yield greater than about 0.38;
placing a ligand for said target receptor in contact with said fluorescent protein fused with said target receptor, wherein,
said ligand is labeled with a label capable of absorbing light emitted by said fluorescent protein, and
said fluorescent protein is a fluorescence energy donor and said label is a fluorescence energy acceptor, or said fluorescent protein is a fluorescence energy acceptor and said label is a fluorescent substance that is a fluorescence energy donor;
irradiating the fluorescence energy acceptor and/or fluorescence energy donor at a wavelength to provide a measurable emission signal; and
measuring the amplitude of the donor's emission and/or emission signal characteristic of the acceptor's emission and the fluorescence energy transfer in order to detect and/or quantify the non-covalent interactions.

13. The method according to claim 12, further comprising:
preparing a cell or cell fragment containing a nucleic acid sequence encoding a fluorescent protein fused with a nucleic acid sequence encoding a target receptor of a cell to produce said fluorescent protein fused with a target receptor of a cell.

14. The method according to claim 13, wherein said placing a ligand for said target receptor in contact with said fluorescent protein fused with said target receptor comprises contacting said ligand with said cell or said cell fragment.

15. The method according to claim 12, wherein said target receptor of a cell is selected from the group consisting of membrane-bound G protein coupled receptors, insulin-like growth factor receptors, ion channel-receptors, and intracellular nuclear receptors.

16. A process for detecting and/or quantifying non-covalent interactions between a target G protein coupled receptor and a G protein, in order to identify the compounds which are biologically active with respect to the receptor, and which are capable of forming a reversible non-covalent interaction with said receptor, wherein:
cells or fragments of cells are prepared containing a nucleic acid sequence encoding for a fluorescent protein fused with a nucleic acid encoding for a receptor coupled to the G proteins, the fusion between the nucleic acid encoding for the fluorescent protein and the nucleic acid encoding for said receptor being so that the properties of the receptor are not modified by the presence of the fluorescent protein, wherein,
the interaction between the target receptor and the G protein is not modified,
the interaction between the target receptor and the biologically active molecule is not modified,
a response transduction function is not modified,
the fluorescent protein is selected from Green Fluorescent Proteins (GFPs) obtained or derived from autofluorescent proteins of Cnidarians, the molar extinction coefficient of which is greater than about 14,000 $M^{-1}$ $cm^{-1}$ and the quantum fluorescence yield of which is greater than about 0.38,
wherein the G protein is labeled with a label selected from:
Green Fluorescent Proteins (GFPs) obtained or derived from autofluorescent proteins of Cnidarions, the the molar extinction coefficient of which is greater than about 14,000 $M^{-1}$ $cm^{-1}$ and the quantum fluorescence yield of which is greater than about 0.38,
fluorescent chemicals compounds, and
non-fluorescent chemical compounds belonging to the Acid Violet group, Acid Red group, alizarins, aluminon, azocarmines, basic fuchsin, Bordeaux R and Carmine,
wherein the fluorescent protein and said label being such that they transfer energy from one to the other, wherein the fluorescent protein is an energy donor or said label is an energy donor,
detecting the interaction between the target receptor labeled with the fluorescent protein and the G protein labeled with said label by fluorescence energy transfer and measuring the fluorescence energy transfer when quantifying the non-covalent interactions.

17. A kit or equipment for detecting and/or quantifying non-covalent interactions between a target receptor labeled with a fluorescent protein and one of its ligands labeled with a label, said kit comprising:
a fluorescent protein selected from Green Fluorescent Proteins (GFPs) obtained or derived from autofluorescent proteins of Cnidarians, the molar extinction coefficient of which is greater than about 14,000 $M^{-1}$ $cm^{-1}$ and the quantum fluorescence yield of which is greater than about 0.38,
the label for the ligand being selected from the group consisting of:
Green Fluorescent Proteins (GFPs) obtained or derived from autofluorescent proteins of Cnidarians, the molar extinction coefficient of which is greater than about 14,000 M⁻¹ cm⁻¹ and the quantum fluorescence yield is greater than about 0.38, fluorescent chemical compounds (eg. Bodipy or coumarin), and non-fluorescent chemical compounds belonging to the Acid Violet group, Acid Red group, alizarins, aluminon, azocarmines, basic fuchsin, Bordeaux R and Carmine, the target receptor fused with a fluorescent protein or a stable cell line which is capable of expressing the target receptor fused with a fluorescent protein or a plasmid containing the nucleic acid sequence coding for said target receptor fused with a fluorescent protein as defined above, and the ligand labeled with selected label.

18. A kit or equipment for detecting and/or quantifying non-covalent interactions between a target receptor labeled with a first fluorescent protein and one of its ligands labeled with a label corresponding to a second fluorescent protein, said first fluorescent protein being chosen from enhanced yellow fluorescent protein (EYFP) or enhanced green fluorescent protein (EGFP) and the ligand being labeled with a second fluorescent protein being enhanced cyan fluorescent protein (ECFP), or said first fluorescent protein being ECFP and the ligand being labeled with EYFP or EGFP, said kit comprising:

a plasmid containing a nucleic acid sequence coding for the target receptor fused with a fluorescent protein, and a plasmid containing a nucleic acid sequence coding for the ligand fused with a second fluorescent protein, or a ligand fused with a second fluorescent protein, obtained via a recombinant route and purified, or a stable cell line which is capable of expressing the target receptor fused with first fluorescent protein, and a stable cell line which is capable of expressing the ligand fused with a second fluorescent protein or a ligand fused with the selected second fluorescent protein.

19. A kit or equipment for detecting and/or quantifying non-covalent interactions between a target receptor consisting of a G protein coupled receptor labeled with a first fluorescent protein and a G protein labeled with a second fluorescent protein, the first fluorescent protein being chosen from enhanced yellow fluorescent protein (EYFP) or enhanced green fluorescent protein (EGFP) and the G protein being labeled with the second fluorescent protein being enhanced cyan fluorescent protein (ECFP) or the first fluorescent protein being ECFP and the G protein being labeled with the second fluorescent protein being selected from EYFP or EGFP, said kit comprising:

a plasmid containing a nucleic acid sequence coding for the receptor fused with the selected first fluorescent protein, and a plasmid containing a nucleic acid sequence coding for the G protein fused with the selected second fluorescent protein, or the G protein fused with the selected second fluorescent protein obtained via a recombinant route and purified, or a stable cell line which is capable of expressing the receptor fused with the selected first fluorescent protein, and a stable cell line which is capable of expressing the G protein fused with the selected second fluorescent protein, or the G protein fused with the selected second fluorescent protein obtained via a recombinant route and purified.

* * * * *